United States Patent
Nguyen et al.

(10) Patent No.: US 11,504,816 B2
(45) Date of Patent: Nov. 22, 2022

(54) SYSTEMS AND METHODS FOR TREATING ANEURYSMS

(71) Applicant: Covidien LP, Mansfield, MA (US)

(72) Inventors: Hoai Nguyen, Westminster, CA (US); Junwei Li, Irvine, CA (US); Andyanhdzung Huynh, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/949,566

(22) Filed: Nov. 3, 2020

(65) Prior Publication Data

US 2021/0128168 A1    May 6, 2021

Related U.S. Application Data

(60) Provisional application No. 62/930,487, filed on Nov. 4, 2019, provisional application No. 62/930,324, filed
(Continued)

(51) Int. Cl.
*B23P 19/04* (2006.01)
*A61B 17/12* (2006.01)
(Continued)

(52) U.S. Cl.
CPC ........ *B23P 19/047* (2013.01); *A61B 17/1214* (2013.01); *A61B 17/12031* (2013.01);
(Continued)

(58) Field of Classification Search
CPC .......... A61B 17/0057; A61B 17/12031; A61B 17/12113; A61B 17/12118;
(Continued)

(56) References Cited

U.S. PATENT DOCUMENTS 5,261,916 A    11/1993 Engelson
5,601,600 A    2/1997 Ton
(Continued)

FOREIGN PATENT DOCUMENTS

CA    3031482 A1    8/2017
CN    105105812 A    12/2015
(Continued)

OTHER PUBLICATIONS

International Search Report and Written Opinion dated Feb. 23, 2021, International Application No. PCT/US20/70743, 14 pages.
(Continued)

*Primary Examiner* — Robert A Lynch
(74) *Attorney, Agent, or Firm* — Fortem IP LLP; Matthew Lincicum

(57) ABSTRACT

Treatment of aneurysms can be improved by delivering an occlusive member (e.g., an expandable braid) to an aneurysm sac in conjunction with an embolic element (e.g., coils, embolic material). A treatment system for such treatment can include an electrolytically corrodible conduit having a proximal portion, a distal portion, and a detachment zone between the proximal portion and the distal portion. An occlusive member having a proximal hub is coupled to the conduit distal portion. The conduit has a lumen configured to pass an embolic element therethrough.

16 Claims, 15 Drawing Sheets

Related U.S. Application Data on Nov. 4, 2019, provisional application No. 62/930,357, filed on Nov. 4, 2019, provisional application No. 62/930,333, filed on Nov. 4, 2019, provisional application No. 62/930,421, filed on Nov. 4, 2019, provisional application No. 62/930,303, filed on Nov. 4, 2019.

(51) Int. Cl.
*A61B 17/00* (2006.01)
*A61B 90/00* (2016.01)

(52) U.S. Cl.
CPC .. *A61B 17/12113* (2013.01); *A61B 17/12145* (2013.01); *A61B 17/12172* (2013.01); *A61B 17/12186* (2013.01); *A61B 17/12168* (2013.01); *A61B 2017/00526* (2013.01); *A61B 2017/00557* (2013.01); *A61B 2017/00862* (2013.01); *A61B 2017/00929* (2013.01); *A61B 2017/12054* (2013.01); *A61B 2017/12063* (2013.01); *A61B 2090/376* (2016.02); *A61B 2090/3966* (2016.02)

(58) Field of Classification Search
CPC .......... A61B 17/1214; A61B 17/12145; A61B 17/12168; A61B 17/12172; A61B 17/12186; A61B 17/1219; A61B 2017/00526; A61B 2017/00575; A61B 2017/00623; A61B 2017/1205; A61B 2017/12054; A61B 2017/12063; A61B 2017/1209; A61F 2/95; A61F 2/962; A61F 2/966; A61F 2/97
USPC ...................................................... 606/213
See application file for complete search history.

(56) References Cited

U.S. PATENT DOCUMENTS

| | | | |
|---|---|---|---|
| 5,916,235 A | 6/1999 | Guglielmi | |
| 6,936,058 B2 | 8/2005 | Forde et al. | |
| 7,128,736 B1 | 10/2006 | Abrams et al. | |
| 7,473,266 B2 | 1/2009 | Glaser | |
| 7,879,065 B2 | 2/2011 | Gesswein et al. | |
| 8,372,062 B2 | 2/2013 | Murphy et al. | |
| 8,690,936 B2 | 4/2014 | Nguyen et al. | |
| 9,339,275 B2 | 5/2016 | Trommeter et al. | |
| 9,713,475 B2 | 7/2017 | Divino et al. | |
| 9,918,718 B2 | 3/2018 | Lorenzo | |
| 10,130,372 B2 | 11/2018 | Griffin | |
| 10,932,933 B2 | 3/2021 | Bardsley et al. | |
| 10,952,740 B2 | 3/2021 | Dasnurkar et al. | |
| 11,076,860 B2 | 8/2021 | Lorenzo | |
| 11,134,953 B2 | 10/2021 | Solaun | |
| 11,179,159 B2 | 11/2021 | Cox et al. | |
| 2001/0000797 A1 | 5/2001 | Mazzocchi | |
| 2004/0176798 A1 | 9/2004 | Foy et al. | |
| 2004/0236344 A1* | 11/2004 | Monstadt | A61B 17/12022 606/108 |
| 2005/0038470 A1 | 2/2005 | Van et al. | |
| 2005/0119684 A1 | 6/2005 | Guterman et al. | |
| 2006/0064151 A1 | 3/2006 | Guterman et al. | |
| 2006/0276824 A1 | 12/2006 | Mitelberg et al. | |
| 2006/0276829 A1 | 12/2006 | Balgobin et al. | |
| 2007/0179520 A1 | 8/2007 | West | |
| 2007/0186933 A1 | 8/2007 | Domingo et al. | |
| 2007/0198075 A1 | 8/2007 | Levy | |
| 2007/0221230 A1 | 9/2007 | Thompson et al. | |
| 2007/0299461 A1 | 12/2007 | Elliott | |
| 2008/0119886 A1 | 5/2008 | Greenhalgh et al. | |
| 2008/0221554 A1 | 9/2008 | Oconnor et al. | |
| 2008/0221703 A1 | 9/2008 | Que et al. | |
| 2008/0281350 A1 | 11/2008 | Sepetka et al. | |
| 2008/0283066 A1 | 11/2008 | Delgado et al. | |
| 2009/0036877 A1 | 2/2009 | Nardone et al. | |
| 2009/0099592 A1 | 4/2009 | Buiser et al. | |
| 2009/0287294 A1 | 11/2009 | Rosqueta et al. | |
| 2010/0023048 A1 | 1/2010 | Mach | |
| 2010/0121350 A1 | 5/2010 | Mirigian | |
| 2011/0144669 A1 | 6/2011 | Becking et al. | |
| 2011/0238041 A1* | 9/2011 | Lim | A61M 25/0054 604/527 |
| 2012/0123510 A1 | 5/2012 | Liungman | |
| 2012/0143301 A1 | 6/2012 | Maslanka et al. | |
| 2013/0066357 A1 | 3/2013 | Aboytes et al. | |
| 2013/0073026 A1 | 3/2013 | Russo et al. | |
| 2013/0138136 A1 | 5/2013 | Beckham et al. | |
| 2013/0211495 A1 | 8/2013 | Halden et al. | |
| 2014/0039542 A1 | 2/2014 | Trommeter et al. | |
| 2014/0135811 A1 | 5/2014 | Divino et al. | |
| 2014/0200607 A1 | 7/2014 | Sepetka et al. | |
| 2014/0215792 A1 | 8/2014 | Leopold et al. | |
| 2014/0257360 A1 | 9/2014 | Keillor | |
| 2015/0005808 A1 | 1/2015 | Chouinard et al. | |
| 2015/0272589 A1 | 10/2015 | Lorenzo | |
| 2015/0313605 A1 | 11/2015 | Griffin | |
| 2015/0335333 A1 | 11/2015 | Jones et al. | |
| 2015/0343181 A1 | 12/2015 | Bradway et al. | |
| 2016/0022445 A1 | 1/2016 | Ruvalcaba et al. | |
| 2016/0106437 A1 | 4/2016 | Van Der Burg et al. | |
| 2016/0128699 A1 | 5/2016 | Hadley et al. | |
| 2016/0331381 A1* | 11/2016 | Ma | B23K 31/02 |
| 2017/0105739 A1 | 4/2017 | Dias et al. | |
| 2017/0156734 A1 | 6/2017 | Griffin | |
| 2017/0224350 A1 | 8/2017 | Shimizu et al. | |
| 2017/0224355 A1 | 8/2017 | Bowman et al. | |
| 2017/0354421 A1 | 12/2017 | Maguire et al. | |
| 2017/0367713 A1* | 12/2017 | Greene, Jr. | A61B 17/12109 |
| 2018/0070955 A1 | 3/2018 | Greene et al. | |
| 2018/0110797 A1 | 4/2018 | Li et al. | |
| 2018/0132856 A1 | 5/2018 | Wierzbicki et al. | |
| 2018/0140305 A1 | 5/2018 | Connor | |
| 2018/0206852 A1 | 7/2018 | Moeller | |
| 2018/0242979 A1 | 8/2018 | Lorenzo | |
| 2018/0256171 A1 | 9/2018 | Chow et al. | |
| 2018/0317932 A1 | 11/2018 | H'Doubler | |
| 2019/0008522 A1 | 1/2019 | Lorenzo | |
| 2019/0009057 A1 | 1/2019 | Li et al. | |
| 2019/0053807 A1 | 2/2019 | Tassoni et al. | |
| 2019/0223876 A1 | 7/2019 | Badruddin et al. | |
| 2019/0223881 A1 | 7/2019 | Hewitt et al. | |
| 2019/0343532 A1 | 11/2019 | Divino et al. | |
| 2019/0351107 A1 | 11/2019 | Sawhney et al. | |
| 2020/0138448 A1 | 5/2020 | Dasnurkar et al. | |
| 2020/0268392 A1 | 8/2020 | Choi et al. | |
| 2021/0128160 A1 | 5/2021 | Li et al. | |
| 2021/0128161 A1 | 5/2021 | Nageswaran et al. | |
| 2021/0128162 A1 | 5/2021 | Rhee et al. | |
| 2021/0128165 A1 | 5/2021 | Pulugurtha et al. | |
| 2021/0128167 A1 | 5/2021 | Patel et al. | |
| 2021/0128169 A1 | 5/2021 | Li et al. | |
| 2021/0129275 A1 | 5/2021 | Nguyen et al. | |
| 2021/0153872 A1 | 5/2021 | Nguyen et al. | |
| 2021/0161643 A1 | 6/2021 | Totten et al. | |
| 2021/0196284 A1 | 7/2021 | Gorochow et al. | |
| 2021/0212698 A1 | 7/2021 | Connor | |
| 2022/0304696 | 9/2022 | Rhee et al. | |

FOREIGN PATENT DOCUMENTS

| | | |
|---|---|---|
| EP | 2468348 B1 | 10/2016 |
| WO | 9905977 A1 | 2/1999 |
| WO | 03011151 A1 | 2/2003 |
| WO | 2007079402 A2 | 7/2007 |
| WO | 2015160721 A1 | 10/2015 |
| WO | 2015166013 A1 | 11/2015 |
| WO | 2018050262 A1 | 3/2018 |
| WO | 2019038293 A1 | 2/2019 |

(56) References Cited

OTHER PUBLICATIONS

International Search Report and Written Opinion dated Apr. 13, 2021, International Application No. PCT/US20/70742, 18 pages.
International Search Report and Written Opinion dated Feb. 17, 2021, International Application No. PCT/US20/70741, 6 pages.

* cited by examiner

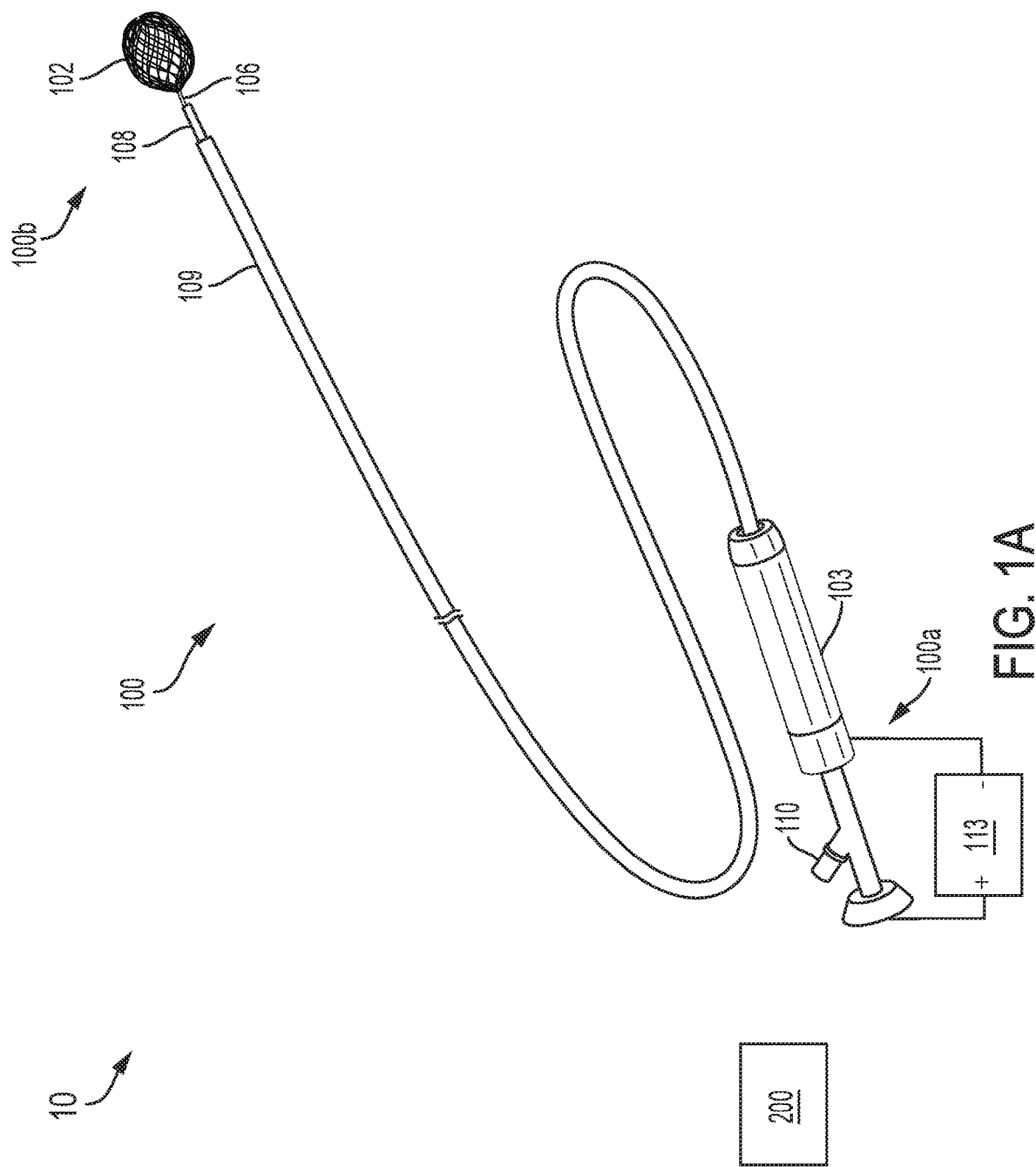

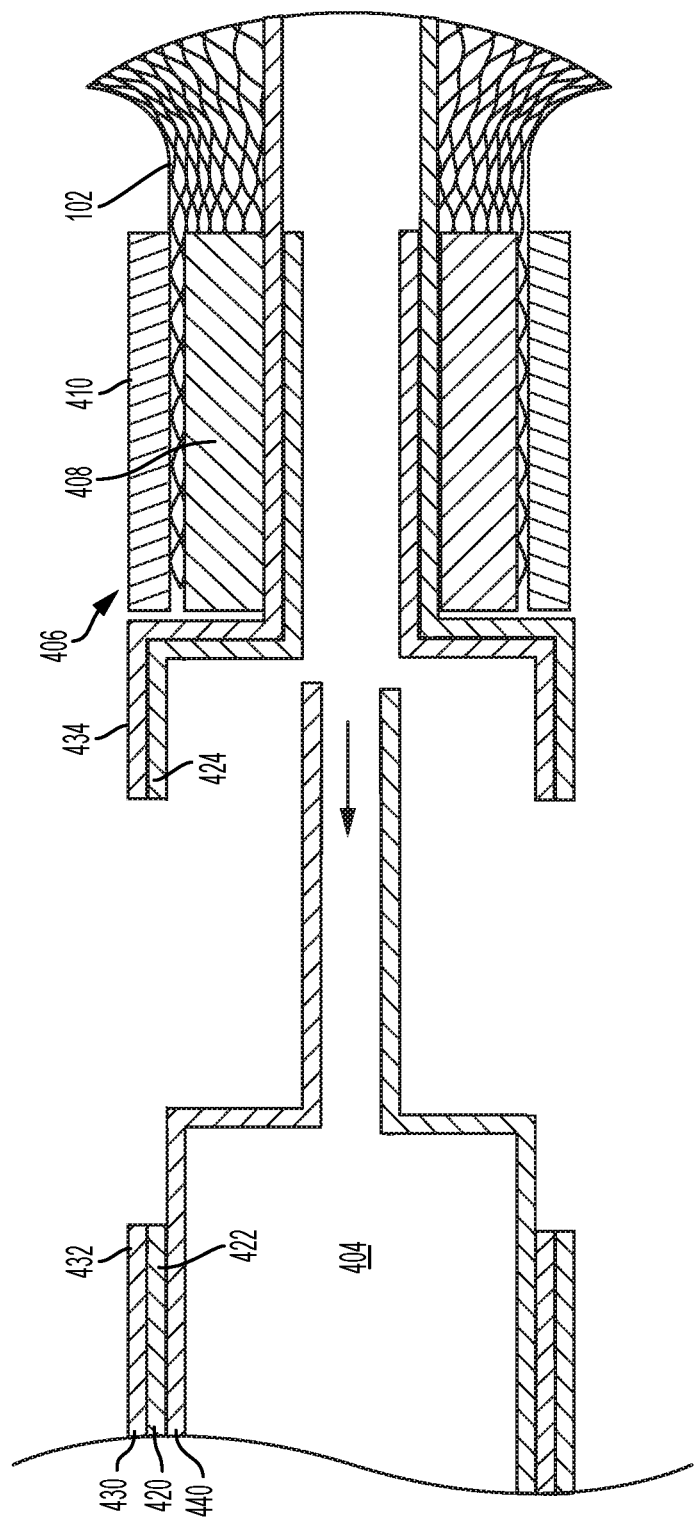

SYSTEMS AND METHODS FOR TREATING ANEURYSMS

CROSS-REFERENCE TO RELATED APPLICATIONS

The present application claims the benefit of priority of U.S. Provisional Application No. 62/930,421, filed Nov. 4, 2019, U.S. Provisional Application No. 62/930,487, filed Nov. 4, 2019, U.S. Provisional Application No. 62/930,303, filed Nov. 4, 2019, U.S. Provisional Application No. 62/930,324, filed Nov. 4, 2019, U.S. Provisional Application No. 62/930,333, filed Nov. 4, 2019, and U.S. Provisional Application No. 62/930,357, filed Nov. 4, 2019, each of which is incorporated by reference herein in its entirety.

The following applications are also incorporated by reference herein in their entireties: U.S. patent application Ser. No. 16/949,567, filed concurrently herewith, and titled DEVICES, SYSTEMS, AND METHODS FOR TREATMENT OF INTRACRANIAL ANEURYSMS; U.S. patent application Ser. No. 16/949,568, filed concurrently herewith, and titled DEVICES, SYSTEMS, AND METHODS FOR TREATMENT OF INTRACRANIAL ANEURYSMS; U.S. patent application Ser. No. 16/949,561, filed concurrently herewith, and titled SYSTEMS AND METHODS FOR TREATING ANEURYSMS; U.S. patent application Ser. No. 16/949,563, filed concurrently herewith, and titled SYSTEMS AND METHODS FOR TREATING ANEURYSMS; U.S. patent application Ser. No. 16/949,564, filed concurrently herewith, and titled SYSTEMS AND METHODS FOR TREATING ANEURYSMS; U.S. patent application Ser. No. 16/949,565, filed concurrently herewith, and titled ANEURYSM TREATMENT DEVICE; U.S. patent application Ser. No. 16/949,569, filed concurrently herewith, and titled DEVICES, SYSTEMS, AND METHODS FOR TREATMENT OF INTRACRANIAL ANEURYSMS; U.S. patent application Ser. No. 16/949,570, filed concurrently herewith, and titled DEVICES, SYSTEMS, AND METHODS FOR TREATING ANEURYSMS; and International Application No. PCT/US20/70743, filed concurrently herewith, titled DEVICES, SYSTEMS, AND METHODS FOR TREATMENT OF INTRACRANIAL ANEURYSMS; International Application No. PCT/US2020/070741, filed concurrently herewith, titled DEVICES, SYSTEMS, AND METHODS FOR TREATMENT OF INTRACRANIAL ANEURYSMS; and International Application No. PCT/US2020/070742, filed concurrently herewith, titled SYSTEMS AND METHODS FOR TREATING ANEURYSMS.

TECHNICAL FIELD

The present technology relates to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated.

One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.
 1. A treatment system comprising:
    an electrolytically corrodible conduit having a proximal portion, a distal portion, a detachment zone between the proximal portion and the distal portion, and a lumen configured to pass an embolic element therethrough; and
    an occlusive member having a proximal hub coupled to the conduit distal portion, the occlusive member configured to be positioned at or adjacent to a treatment site.
 2. The treatment system of any one of the Clauses herein, wherein the detachment zone comprises a portion of the conduit configured to be severed in response to delivery of electrical current thereto.

3. The treatment system of any one of the Clauses herein, wherein the detachment zone is axially between the conduit proximal portion and the conduit distal portion 4. The treatment system of any one of the Clauses herein, wherein the conduit comprises a sidewall having one or more apertures formed therein within the detachment zone.

5. The treatment system of any one of the Clauses herein, wherein the conduit comprises a sidewall having a reduced thickness in the detachment zone.

6. The treatment system of any one of the Clauses herein, wherein the conduit has a lower material density in the detachment zone than in the proximal and distal portions.

7. The treatment system of any one of the Clauses herein, wherein the detachment zone has a microstructure with lower crystallinity than each of the conduit proximal portion and the conduit distal portion.

8. The treatment system of any one of the Clauses herein, wherein the detachment zone has a microstructure that is more amorphous than each of the conduit proximal portion and the conduit distal portion.

9. The treatment system of any one of the Clauses herein, wherein the conduit is electrically conductive.

10. The treatment system of any one of the Clauses herein, wherein the conduit is metallic.

11. The treatment system of any one of the Clauses herein, wherein the conduit comprises a hypotube.

12. The treatment system of any one of the Clauses herein, wherein the conduit comprises a catheter.

13. The treatment system of any one of the Clauses herein, wherein the conduit has a wall thickness of between about 0.0005 inches and about 0.0015 inches, or about 0.001 inches.

14. The treatment system of any one of the Clauses herein, wherein the conduit has an outer diameter of less than about 0.027 inches, less than about 0.021 inches, less than about 0.017 inches, or less than about 0.015 inches.

15. The treatment system of any one of the Clauses herein, wherein the conduit has an inner diameter of less than about 0.015 inches, less than about 0.012 inches, less than about 0.010 inches, or less than about 0.008 inches.

16. The treatment system of any one of the Clauses herein, further comprising a liner extending through the conduit lumen.

17. The treatment system of any one of the Clauses herein, wherein the liner comprises an elongate tubular member having a lumen configured to pass an embolic element therethrough.

18. The treatment system of any one of the Clauses herein, wherein the liner is slidably disposed within the conduit lumen.

19. The treatment system of any one of the Clauses herein, wherein the liner is electrically insulative.

20. The treatment system of any one of the Clauses herein, wherein the liner comprises a polymer.

21. The treatment system of any one of the Clauses herein, wherein the liner comprises polytetrafluoroethylene (PTFE).

22. The treatment system of any one of the Clauses herein, wherein the liner has a wall thickness of between about 0.0005 inches and about 0.0015 inches, or about 0.001 inches.

23. The treatment system of any one of the Clauses herein, wherein the liner has an outer diameter of less than about 0.027 inches, less than about 0.021 inches, less than about 0.017 inches, or less than about 0.010 inches.

24. The treatment system of any one of the Clauses herein, wherein the liner has an inner diameter of less than about 0.015 inches, less than about 0.012 inches, less than about 0.010 inches, less than about 0.008 inches, or less than about 0.006 inches.

25. The treatment system of any one of the Clauses herein, wherein the liner has a sidewall that is continuous along the detachment zone.

26. The treatment system of any one of the Clauses herein, wherein when the liner is disposed within the conduit, a distal end of the liner extends distally of a distal end of the conduit.

27. The treatment system of any one of the Clauses herein, wherein when the liner is disposed within the conduit, a distal end of the liner is substantially coterminous with a distal end of the conduit.

28. The treatment system of any one of the Clauses herein, wherein the liner is configured to be slidably retracted with respect to the occlusive member following severance of the detachment zone.

29. The treatment system of any one of the Clauses herein, further comprising a sheath extending over the conduit.

30. The treatment system of any one of the Clauses herein, wherein the sheath is electrically insulative.

31. The treatment system of any one of the Clauses herein, wherein the sheath comprises a polymer.

32. The treatment system of any one of the Clauses herein, wherein the sheath comprises polytetrafluoroethylene (PTFE).

33. The treatment system of any one of the Clauses herein, wherein the sheath has a wall thickness of between about 0.0005 inches and about 0.002 inches, or about 0.0015 inches.

34. The treatment system of any one of the Clauses herein, wherein the sheath has an outer diameter of less than about 0.027 inches, less than about 0.021 inches, less than about 0.017 inches, or less than about 0.010 inches.

35. The treatment system of any one of the Clauses herein, wherein the sheath has an inner diameter of less than about 0.015 inches, less than about 0.012 inches, or less than about 0.010 inches.

36. The treatment system of any one of the Clauses herein, wherein the sheath comprises a proximal portion extending over the conduit proximal portion and a distal portion extending over the conduit distal portion.

37. The treatment system of any one of the Clauses herein, wherein the sheath comprises a gap between the proximal portion and the distal portion.

38. The treatment system of any one of the Clauses herein, wherein the sheath proximal portion and the sheath distal portion are discrete segments spaced apart from one another by a gap.

39. The treatment system of any one of the Clauses herein, wherein the gap between the sheath proximal portion and the sheath distal portion is axially aligned with the detachment zone.

40. The treatment system of any one of the Clauses herein, wherein the sheath does not extend fully over the conduit detachment zone.

41. The treatment system of any one of the Clauses herein, wherein the sheath proximal portion is configured to be proximally retracted with respect to the occlusive member following severance of the conduit at the detachment zone.

42. The treatment system of any one of the Clauses herein, wherein the sheath distal portion is fixedly coupled to the occlusive member.

43. The treatment system of any one of the Clauses herein, wherein the sheath distal portion extends distally beyond the hub of the occlusive member.

44. The treatment system of any one of the Clauses herein, wherein the sheath distal portion extends distally beyond a distal end of the occlusive member.

45. The treatment system of any one of the Clauses herein, wherein the sheath distal portion extends distally beyond a distal end of the conduit.

46. The treatment system of any one of the Clauses herein, wherein the sheath distal portion extends distally beyond a distal end of the liner.

47. The treatment system of any one of the Clauses herein, wherein a distal portion of the conduit is configured to be disposed at or adjacent the treatment site along with the occlusive member.

48. The treatment system of any one of the Clauses herein, wherein the treatment site comprises an aneurysm sac.

49. The treatment system of any one of the Clauses herein, wherein the conduit has a distal portion having a smaller cross-sectional dimension than a proximal portion of the conduit.

50. The treatment system of any one of the Clauses herein, wherein the occlusive member is coupled to the conduit via one or more bands or clamps.

51. The treatment system of any one of the Clauses herein, wherein the one or more bands or clamps circumferentially surround both the conduit and a proximal portion of the occlusive member.

52. The treatment system of any one of the Clauses herein, wherein the occlusive member is coupled to the conduit via an adhesive.

53. The treatment system of any one of the Clauses herein, wherein the occlusive member is an occlusive member or intrasaccular device configured to be implanted within an aneurysm.

54. The treatment system of any one of the Clauses herein, wherein the occlusive member comprises an expandable mesh having a constrained state for delivery to an aneurysm and an expanded state in which at least a portion of the mesh is configured to be disposed across a neck of the aneurysm.

55. The treatment system of any one of the Clauses herein, wherein the expandable mesh comprises a plurality of braided filaments that assume a pre-set, three-dimensional shape in the expanded state.

56. The treatment system of any one of the Clauses herein, wherein the expandable mesh comprises a braid formed of 24, 32, 36, 48, 64, or 72 filaments.

57. The treatment system of any one of the Clauses herein, wherein the expandable mesh comprises a braid formed of a plurality of wires, some or all of which have a diameter of at least 0.001 inches.

58. The treatment system of any one of the Clauses herein, wherein the expandable mesh comprises a braid formed of a plurality of wires, some or all of which have the same diameter.

59. The treatment system of any one of the Clauses herein, wherein the expandable mesh comprises a braid formed of a plurality of wires, at least some of which have different diameters.

60. The treatment system of any one of the Clauses herein, wherein, in the expanded state, the expandable mesh forms one of a sphere, a prolate spheroid, or an oblate spheroid.

61. The treatment system of any one of the Clauses herein, wherein the expandable mesh comprises an inner layer and an outer layer.

62. The treatment system of any one of the Clauses herein, wherein the expandable mesh has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

63. The treatment system of any one of the Clauses herein, wherein the expandable mesh is a laser-cut tube.

64. The treatment system of any one of the Clauses herein, wherein the expandable mesh comprises a plurality of interwoven filaments.

65. The treatment system of any one of the Clauses herein, wherein the occlusive member is curved along at least a majority of its entire length.

66. The treatment system of any one of the Clauses herein, wherein the occlusive member is collapsible when contacted by an embolic element.

67. The treatment system of any one of the Clauses herein, wherein the occlusive member is collapsible when contacted by a synthetic gel or fluid.

68. The treatment system of any one of the Clauses herein, wherein the occlusive member is configured to rotate about the conduit.

69. The treatment system of any one of the Clauses herein, wherein the occlusive member is rotatably and slidably coupled to the conduit.

70. The treatment system of any one of the Clauses herein, wherein the occlusive member has an aperture at a distal portion thereof, and wherein the conduit extends through the aperture.

71. The treatment system of any one of the Clauses herein, wherein the occlusive member has an aperture at a distal portion thereof, and wherein the liner extends through the aperture.

72. The treatment system of any one of the Clauses herein, wherein the occlusive member has an aperture at a distal portion thereof, and wherein the sheath extends through the aperture.

73. The treatment system of any one of the Clauses herein, wherein the embolic element is a liquid embolic.

74. The treatment system of any one of the Clauses herein, wherein the embolic element comprises a biopolymer and/or a chemical crosslinking agent.

75. The treatment system of any one of the Clauses herein, wherein the biopolymer includes chitosan, a derivative of chitosan, an analog of chitosan, or a combination thereof.

76. The treatment system of any one of the Clauses herein, wherein the chemical crosslinking agent includes genipin, a derivative of genipin, an analog of genipin, or a combination thereof.

77. A system comprising:
the treatment system of any one of the Clauses herein; and
an elongated shaft having a lumen extending therethrough, wherein the treatment system is configured to be slidably disposed within the lumen of the elongated shaft.

78. A system comprising:
the treatment system of any one of the Clauses herein;
a first elongated shaft having a first lumen extending therethrough, wherein the treatment system is configured to be slidably disposed within the first lumen; and
a second elongated shaft having a second lumen extending therethrough, wherein the first elongated shaft is configured to be slidably disposed within the second lumen.

79. The system of 78, wherein the first elongated shaft is a microcatheter and the second elongated shaft is a delivery or guide catheter.

80. The system of any one of the Clauses herein, wherein the microcatheter has a nominal inner diameter of about 0.015 inches or less, about 0.017 inches or less, about 0.021 inches or less, or about 0.027 inches or less.

81. A method for treating an aneurysm, comprising:
providing the treatment system of any one of the Clauses herein.

82. The method of any one of the Clauses herein, further comprising:
positioning a distal end of the conduit in an aneurysm cavity; and
releasing the occlusive member from the conduit while the distal end of the conduit is positioned within the aneurysm cavity such that the occlusive member self-expands to assume an expanded state.

83. The method of any one of the Clauses herein, wherein releasing the occlusive member comprises electrolytically corroding the detachment zone of the conduit.

84. The method of 82 one of the previous Clauses, wherein releasing the occlusive member comprises delivering electrical current to the conduit.

85. The method of any one of the Clauses herein, wherein positioning the distal end of the conduit comprises advancing the distal end of the conduit toward a dome or distalmost end of the aneurysm, such that the distal end of the conduit extends beyond a distal terminus of a microcatheter surrounding the conduit.

86. The method of any one of the Clauses herein, wherein positioning the distal end of the conduit comprises advancing the distal end of the liner toward a dome or distalmost end of the aneurysm, such that the distal end of the liner extends beyond a distal terminus of a microcatheter surrounding the conduit.

87. The method of any one of the Clauses herein, further comprising positioning a distal end of the conduit, sheath, and/or liner in the aneurysm cavity along with the occlusive member.

88. The method of any one of the Clauses herein, further comprising proximally retracting the liner with respect to the conduit distal portion.

89. The method of any one of the Clauses herein, further comprising removing the liner from within the lumen of the conduit.

90. The method of any one of the Clauses herein, wherein releasing the occlusive member comprises allowing the occlusive member to self-expand to assume a first expanded state in which the occlusive member forms a first shape, wherein, in the first expanded state, the occlusive member encloses an interior region having a first interior volume, the method further comprising
delivering an embolic element between the occlusive member and the aneurysm wall to transform the occlusive member into a second expanded state in which the occlusive member defines a second interior volume less than the first interior volume, wherein the occlusive member forms a second shape in the second expanded state that is different than the first shape in the first expanded state.

91. The method of any one of the Clauses herein, wherein transforming the occlusive member into the second expanded shape includes injecting the embolic element to urge a portion of a sidewall of the expandable mesh in a direction away from a wall of the aneurysm and towards the interior region of the occlusive member.

92. The method of any one of the Clauses herein, wherein transforming the occlusive member into the second expanded shape includes injecting the embolic element to invert a portion of a sidewall of the occlusive member such that the portion is convex towards the aneurysm wall in the first expanded state and concave towards the aneurysm wall in the second expanded state.

93. The method of any one of the Clauses herein, wherein the embolic element comprises a liquid embolic.

94. The method of any one of the Clauses herein, wherein the embolic element comprises one or more embolization coils.

95. The method of any one of the Clauses herein, wherein delivering the embolic element occurs after the occlusive member is in the first expanded state.

96. The method of any one of the Clauses herein, wherein the occlusive member is a mesh.

97. The method of any one of the Clauses herein, wherein the occlusive member is a braid.

98. The method of any one of the Clauses herein, wherein the occlusive member is a dual-layered braid.

99. The method of any one of the Clauses herein, wherein the occlusive member has a globular or generally spherical shape in the first expanded state.

100. The method of any one of the Clauses herein, wherein the occlusive member is cup or bowl-shaped in the second expanded state.

101. The method of any one of the Clauses herein, wherein the second shape is a predetermined three-dimensional shape.

102. The method of any one of the Clauses herein, wherein the occlusive member forms a multi-layer braid at the neck of the aneurysm in the second expanded state.

103. The method of any one of the Clauses herein, wherein the occlusive member comprises a plurality of braided filaments that assume a pre-set, three-dimensional shape in the expanded state.

104. The method of any one of the Clauses herein, wherein the occlusive member comprises a braid formed of 24, 32, 36, 48, 64, or 72 filaments.

105. The method of any one of the Clauses herein, wherein the occlusive member comprises a braid formed of a plurality of wires, some or all of which have a diameter of about 0.001 inches (0.00254 cm).

106. The method of any one of the Clauses herein, wherein the occlusive member comprises a braid formed of a plurality of wires, some or all of which have the same diameter.

107. The method of any one of the Clauses herein, wherein the occlusive member comprises a braid formed of a plurality of wires, at least some of which have different diameters.

108. The method of any one of the Clauses herein, wherein the occlusive member forms a closed, globular shape in the expanded state, the mesh having an aperture at a distal portion.

109. The method of any one of the Clauses herein, wherein, in the expanded state, the occlusive member forms one of a sphere, a prolate spheroid, or an oblate spheroid.

110. The method of any one of the Clauses herein, wherein the occlusive member comprises an inner layer and an outer layer.

111. The method of any one of the Clauses herein, wherein the occlusive member comprises an inner layer and an outer layer that meet at a fold at a distal portion of the occlusive member.

112. The method of any one of the Clauses herein, wherein the expandable mesh includes an aperture at a distal portion, the aperture being defined by the fold.

113. The method of any one of the Clauses herein, wherein the occlusive member comprises an inner layer and an outer layer that meet at a fold at a proximal portion of the occlusive member.

114. The method of any one of the Clauses herein, wherein the expandable mesh includes an aperture at a distal portion, the aperture being defined by the fold.

115. The method of any one of the Clauses herein, wherein the occlusive member has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

116. The method of any one of the Clauses herein, wherein the occlusive member is formed of a plurality of filaments having first and second ends fixed at the hub or a coupler.

117. The method of any one of the Clauses herein, wherein the occlusive member is formed of a plurality of filaments formed of an inner core material surrounded by an outer material.

118. The method of any one of the Clauses herein, wherein the inner core material is a radiopaque material and the outer material is a superelastic material.

119. The method of any one of the Clauses herein, wherein the occlusive member is a laser-cut tube.

120. The method of any one of the Clauses herein, wherein the occlusive member comprises a plurality of filaments.

121. The method of any one of the Clauses herein, wherein the filaments are interwoven.

122. The method of any one of the Clauses herein, wherein the filaments are braided.

123. The method of any one of the Clauses herein, wherein each of the filaments has a first end and a second end opposite the first end, and wherein both the first and second ends of the filaments are fixed relative to one another at a coupler.

124. The method of any one of the Clauses herein, wherein the coupler is disposed at a distal end of the occlusive member.

125. The method of any one of the Clauses herein, wherein the coupler is disposed at a proximal end of the occlusive member.

126. The method of any one of the Clauses herein, wherein each of the filaments terminate at only one end of the occlusive member.

127. The method of any one of the Clauses herein, wherein the filaments form an opening at an end of the occlusive member opposite the only one end.

128. The method of any one of the Clauses herein, wherein an inverted portion of each of the filaments define the opening.

129. The method of any one of the Clauses herein, wherein the inverted portions of the filaments are configured to move relative to one another.

130. The method of any one of the Clauses herein, wherein the embolic element comprises a biopolymer and a chemical crosslinking agent.

131. The method of any one of the Clauses herein, wherein the biopolymer includes chitosan, a derivative of chitosan, an analog of chitosan, or a combination thereof.

132. The method of any one of the Clauses herein, wherein the chemical crosslinking agent includes genipin, a derivative of genipin, an analog of genipin, or a combination thereof.

133. The method of any one of the Clauses herein, wherein the embolic element further comprises a physical crosslinking agent.

134. The method of any one of the Clauses herein, the physical crosslinking agent includes β glycerophosphate, a derivative of β glycerophosphate, an analog of β glycerophosphate, or a combination thereof.

135. The method of any one of the Clauses herein, wherein
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β glycerophosphate, a derivative of β glycerophosphate, an analog of β glycerophosphate, or a combination thereof.

136. The method of any one of the Clauses herein, wherein the embolic element comprises a contrast agent.

137. The method of any one of the Clauses herein, wherein the contrast agent is selected to provide diminishing radiopacity.

138. The method of any one of the Clauses herein, wherein the contrast agent includes iohexol, a derivative of iohexol, an analog of iohexol, or a combination thereof.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1A shows a perspective view of a system for treating an aneurysm in accordance with the present technology.

FIG. 4C shows a schematic side cross-sectional view of the treatment system of FIG. 4B after electrolytic detachment.

DETAILED DESCRIPTION

Figure 1B:
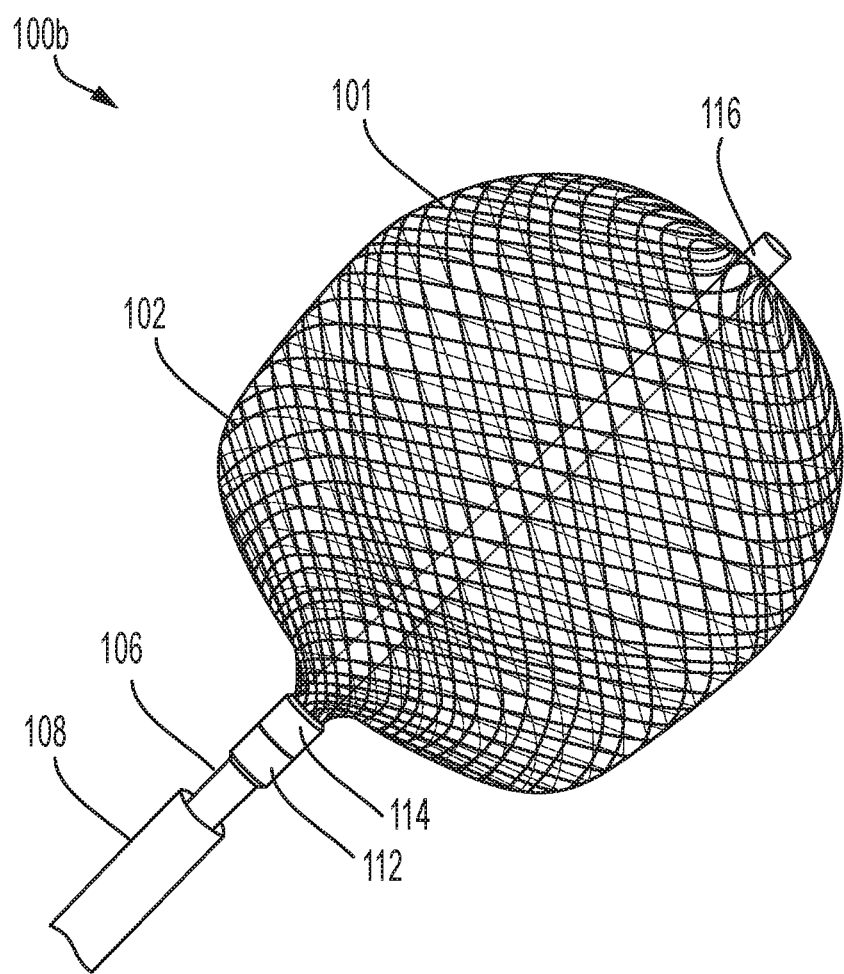
FIG. 1B shows an enlarged view of a distal portion of the treatment system of FIG. 1A in accordance with the present technology.

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Once the occlusive member has deployed within the aneurysm and the embolic element has been delivered, the occlusive member may be detached from the delivery assembly. Suitable detachment mechanisms must be as small as possible so as to be guided through the fine bore of the catheter to the treatment site, while on the other hand they must securely and reliably produce detachment of the intrasaccular implant. Absent a reliable detachment of the intrasaccular implant, withdrawal of the delivery conduit and catheter may cause unintended removal of the occlusive member from the cavity to be occluded and thus injure and/or rupture of the wall of the cavity or vessel. In some embodiments, an electrolytic detachment mechanism as described herein can be used to facilitate reliable, controlled detachment of the occlusive member.

The occlusive member can be implanted in body cavities or blood vessels. In addition to the occlusive member, the treatment system can comprise a voltage source, a cathode, a delivery conduit, and a catheter. The occlusive member and the delivery conduit can be coupled together such that both can be slid in the catheter in the longitudinal direction. For example, the occlusive member can be coupled to a distal portion of the conduit, and the conduit can include a detachment zone configured to be electrolytically severed. In some embodiments, the conduit can be adapted to serve as an anode, such that a portion of the conduit is designed to be electrolytically corroded at one or more points so that while in contact with a body fluid, and the occlusive member may be released from the conduit. The delivery conduit can be configured to pass one or more embolic elements therethrough for intrasaccular delivery. The embolic element may be passed through the conduit and delivered to the treatment site. Once the occlusive member and any embolic elements are deployed, current can be applied to the conduit to electrolytically corrode the conduit at the detachment zone. After the conduit has been severed at the detachment zone, the conduit can be retracted, and the occlusive member may remain in position at the treatment site. In some embodiments, an inner liner and/or an outer sheath extend along at least a portion of the length of the conduit. The outer sheath can include a gap or opening that is aligned with the detachment zone such that the detachment zone of the conduit is exposed to bodily fluids while at the treatment site.

Specific details of systems, devices, and methods for treating intracranial aneurysms in accordance with embodiments of the present technology are described herein with reference to FIGS. 1A-8C. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. OVERVIEW OF SYSTEMS OF THE PRESENT TECHNOLOGY

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100a configured to be extracorporeally positioned during treatment and a distal portion 100b configured to be intravascularly positioned within a blood vessel (such as an intracranial blood vessel) at a treatment site at or proximate an aneurysm. The treatment system 100 may include a handle 103 at the proximal portion 100a, the occlusive member 102 at the distal portion 100b, and a plurality of elongated shafts or members extending between the proximal and distal portions 100a and 100b. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

FIG. 1B is an enlarged view of the distal portion 100b of the treatment system 100. Referring to FIGS. 1A and 1B together, the occlusive member 102 may be detachably coupled to a distal portion of the elongated member 106. For example, the elongated member 106 may include a first coupler 112, and the occlusive member 102 may include a second coupler 114 configured to detachably couple with the first coupler 112. In some embodiments, the couplers 112, 114 can take the form of an electrolytic detachment mechanism, for example as described in more detail below with respect to FIGS. 4-8C. The treatment system 100 may further comprise a conduit 116 extending from the handle 103 (for example, via port 110) distally to the distal portion 100b of the treatment system 100. The conduit 116 is configured to deliver the embolic element (and/or one or more precursors thereof) through one or more components of the delivery system (e.g., the first or second elongated shafts 109, 108, the elongated member 106, etc.) to a position at the exterior of the occlusive member 102. As such, the embolic element may be positioned between the occlusive member 102 and an inner wall of the aneurysm cavity, as described in greater detail below. In some embodiments, the elongated member 106 serves as the conduit 116.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongated shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise an elongated tubular member having a lumen therein, for example a conduit. In some embodiments, the elongated member 106 may comprise any other suitable form such as a solid metal wire, an elongated tubular shaft, or any combination thereof.

In some embodiments, the elongated member 106 can comprise stainless steel, nitinol, or other metal or alloy. In some embodiments, the elongated member 106 can be surrounded over some or all of its length by a coating, such as, for example, polytetrafluoroethylene. In some examples, the elongated member 106 can be a hypotube or other conductive tubular member, and can include an outer insulative sheath and/or an inner insulative liner extending along a length of the elongated member 106. The elongated member 106 may have a diameter that is generally constant along its length, or the elongated member 106 may have a diameter that tapers radially inwardly, along at least a portion of its length, as it extends in a distal direction.

A power supply 113 may be coupled to a proximal portion of the elongated shaft 108, which can take the form of a conductive wire. The power supply 113 may also be coupled to a proximal portion of a handle or to the patient. A current can flow from the power supply 113, to a detachment zone at or near the occlusive member 102, and to a return path via the first elongated shaft 109, the second elongated shaft 108, and/or another structure extending near the detachment zone. Alternatively, the current from the detachment zone may flow to the patient, and subsequently to ground or to the power supply 113. Power supply 113, for example, may be a direct current power supply, an alternating current power supply, or a power supply switchable between a direct current and an alternating current. A positive terminal of a direct current power supply, as shown in FIG. 1, may be coupled to the proximal portion of the elongated shaft 108, 111 and a negative terminal of a direct current power supply may be coupled to the proximal portion of the handle. Power supply 113 may provide a current through the treatment system 100 to initiate an electrolytic process during use of the assembly in a fluid medium such as a bloodstream, which may be used as an electrolyte. A power supply, such as an alternating or direct current power supply, may additionally be used to initiate an electrothrombosis process.

A. Selected Examples of Occlusive Members

Figure 1C:
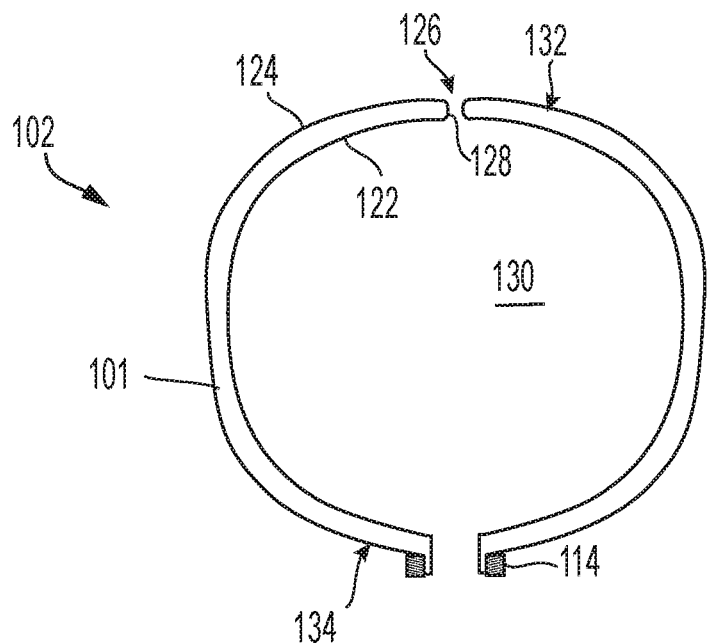
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
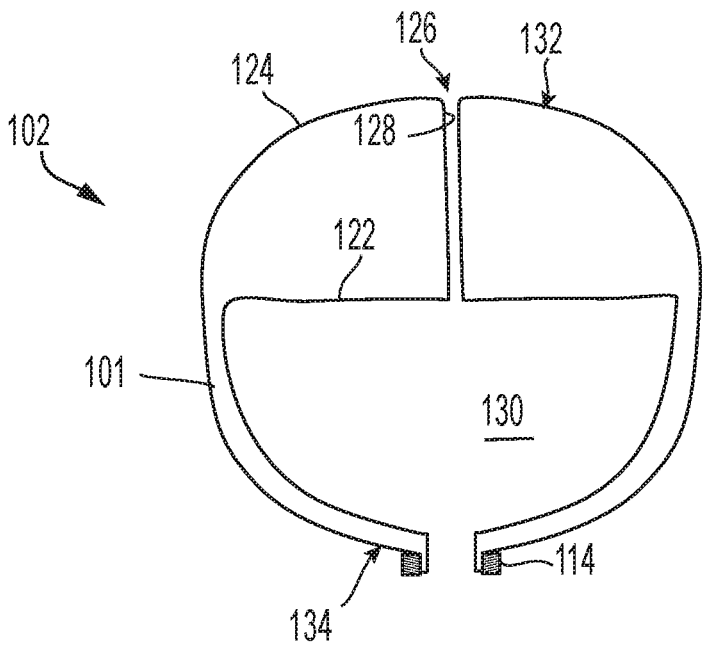
Figure 2:
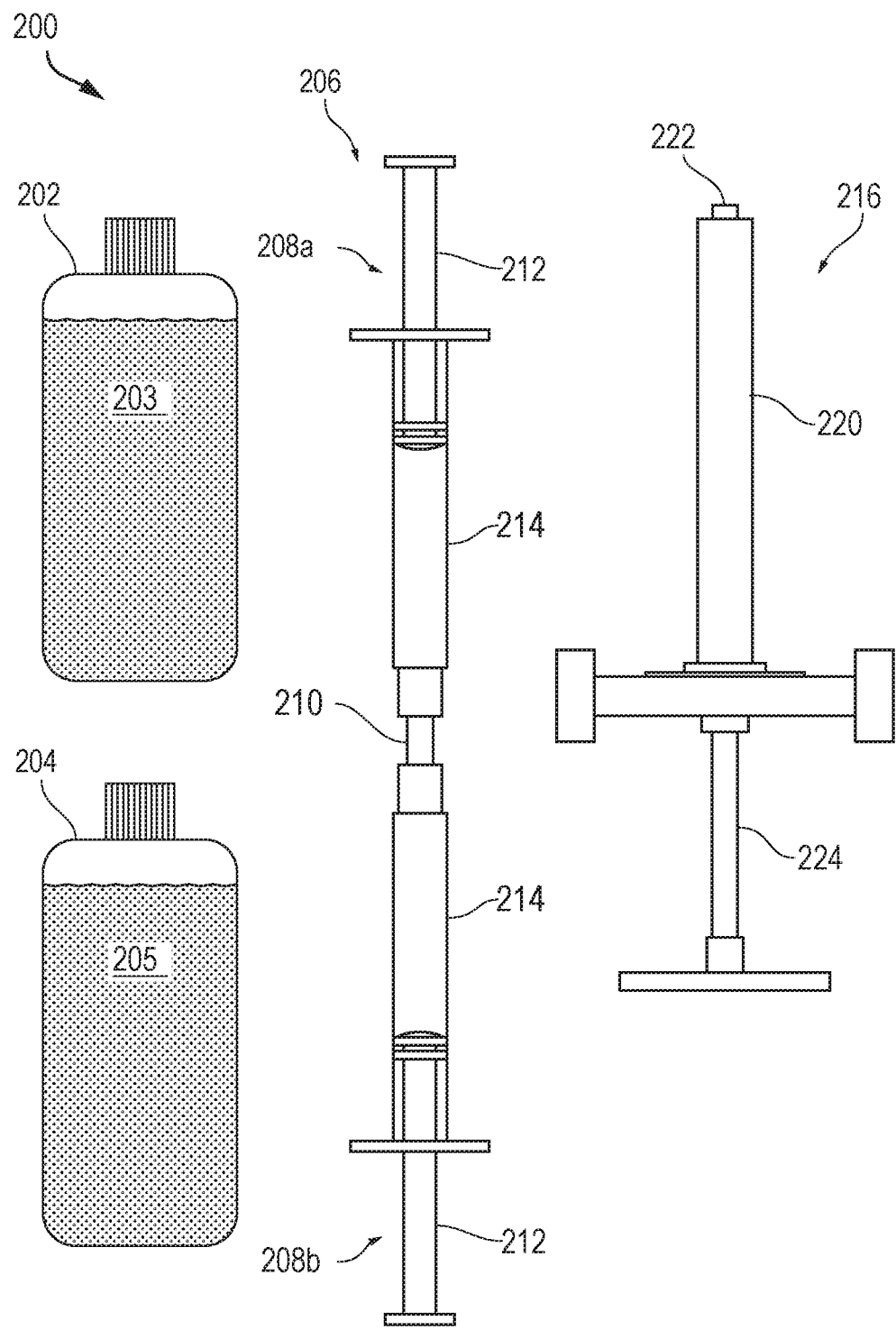
FIG. 2 shows an embolic kit according to the present technology.

The inner layer 124 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusion member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to the at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208a, 208b) and a coupler 210 extending between respective exit ports (not shown) of the mixing syringes 208. The mixing syringes 208a, 208b each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100b of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the kit 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include β glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

Additional details regarding suitable embolic element may be found in U.S. patent application Ser. No. 15/299,929, filed Oct. 21, 2016, the disclosure of which is incorporated herein by reference in its entirety.

II. SELECTED METHODS FOR TREATING ANEURYSMS

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state. Releasing the occlusive member 102 from the shaft 108 and allowing the occlusive member 102 to self-expand into a first expanded state may alternatively, or additionally, include withdrawing shaft 108 relative to the elongated member 106.

Figure 3A:
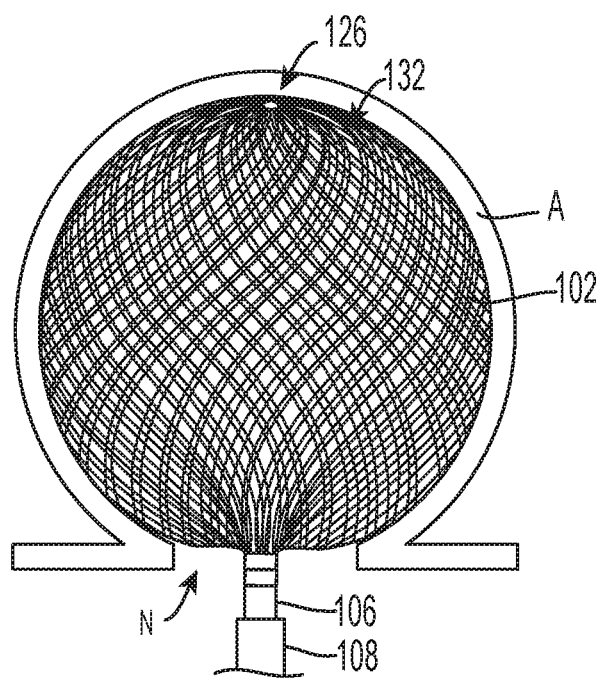
FIGS. 3A-3G depict an example method of treating an aneurysm with the treatment system of the present technology.
Figure 3B:
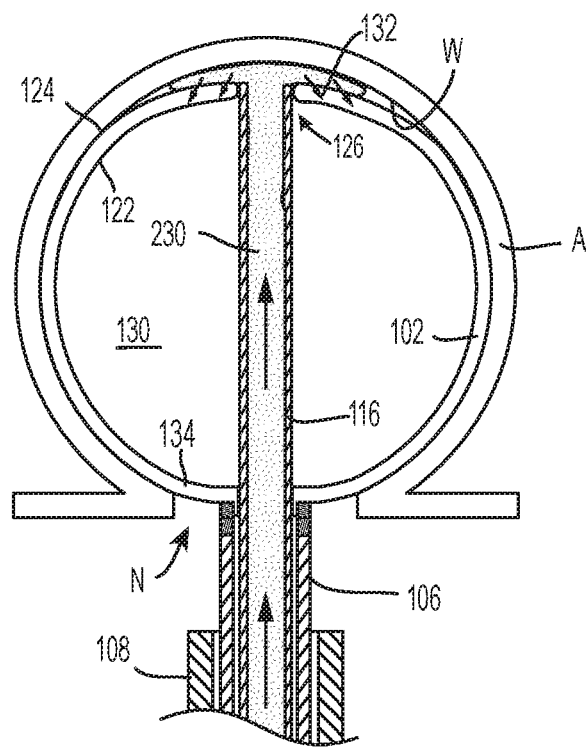

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W. Although the illustrated example shows a separate conduit 116 extending through a lumen of the elongated member 106, in other embodiments the elongated member 106 may itself form the conduit 116, e.g., by extending through a proximal hub of the occlusive member 102 and through the internal volume 130.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
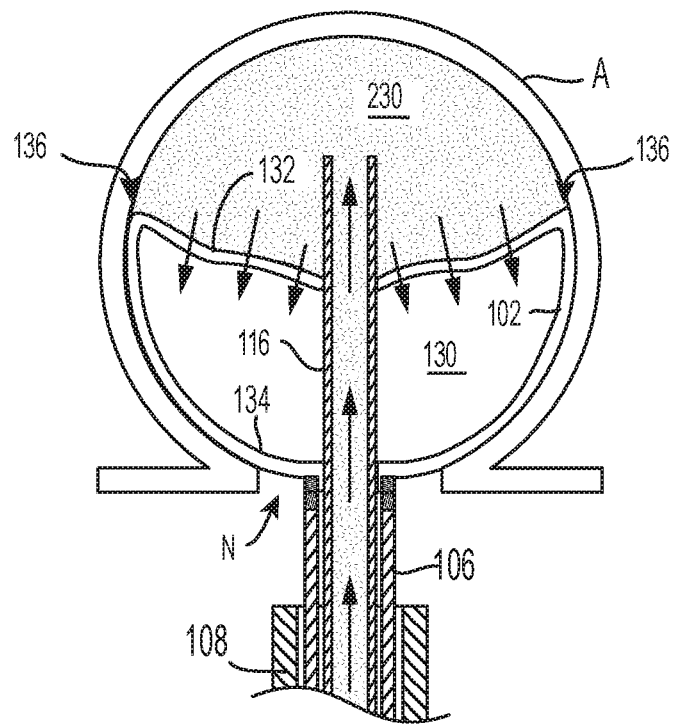
Figure 3D:
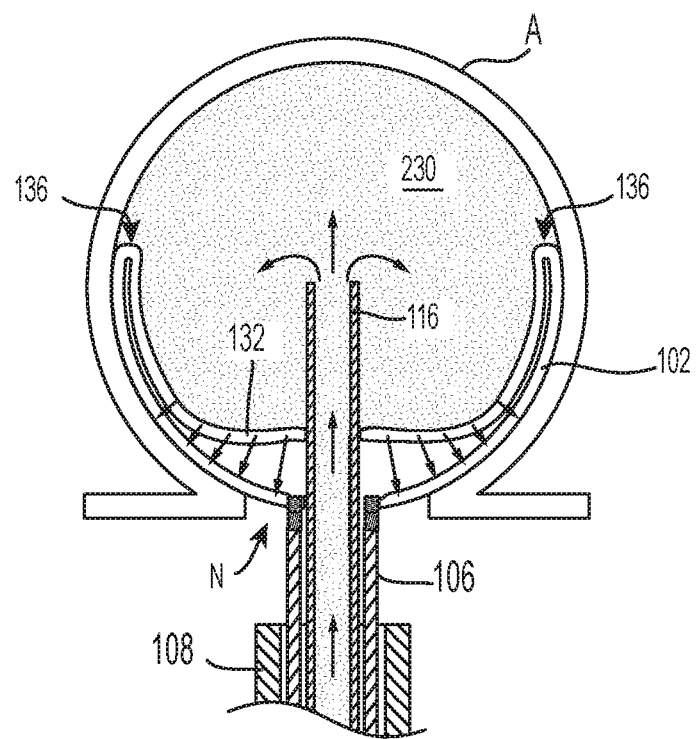

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figure 3E:
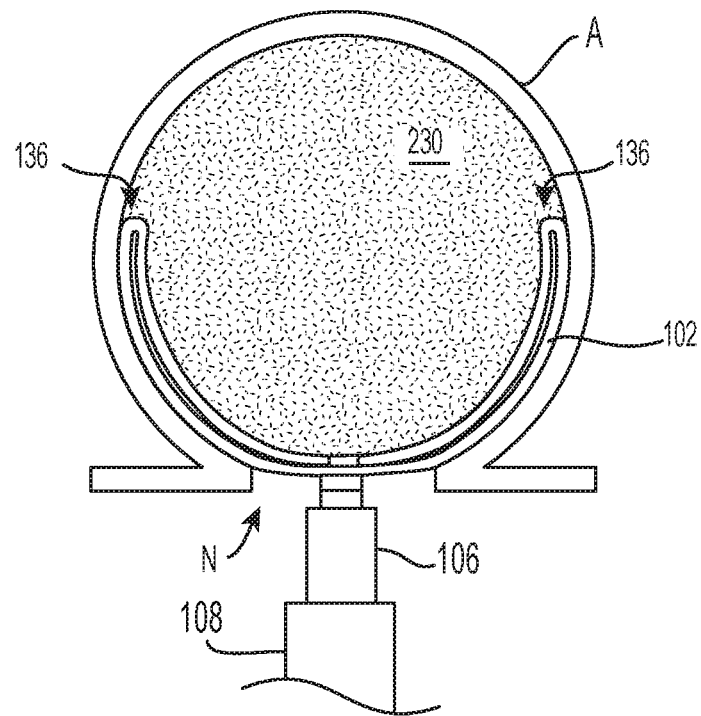
Figure 3F:
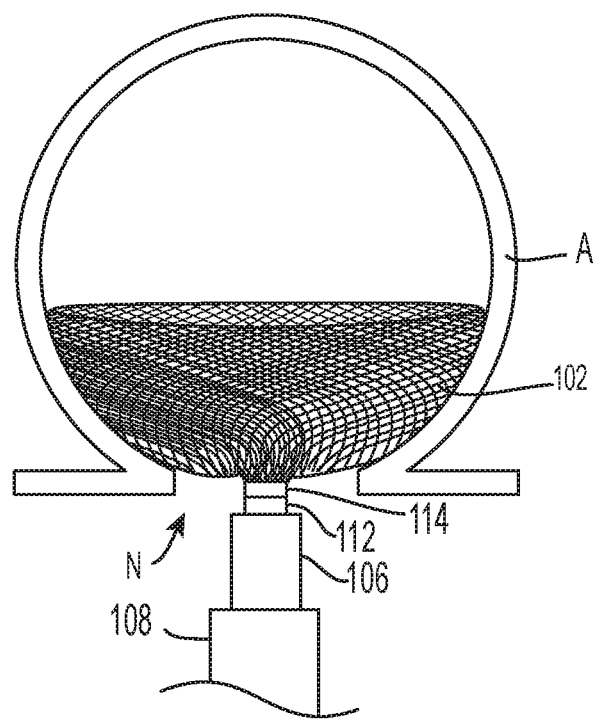

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusion member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
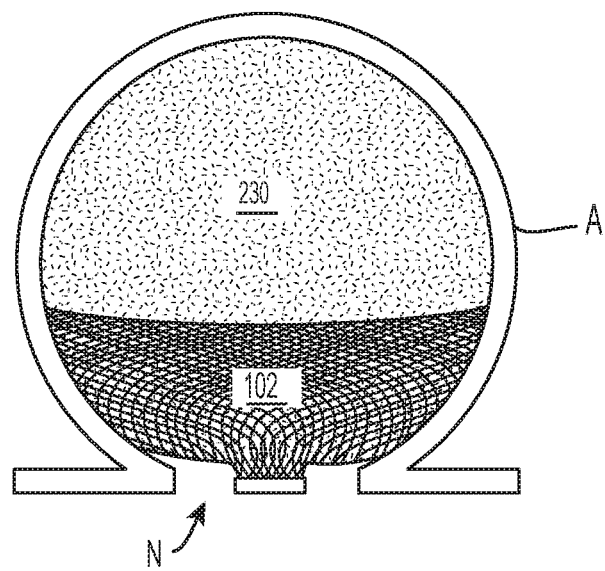

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A. For example, the occlusive member 102 may be detached from the elongated member 106 using any of the electrolytic detachment mechanisms described in more detail below. In some examples, at least a distal portion of the conduit 116 may remain in place following detachment (e.g., electrolytic severance) of the elongated member 106 and/or conduit 116.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive member 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. EXAMPLE SYSTEMS WITH ELECTROLYTIC DETACHMENT MECHANISMS

Figure 4A:
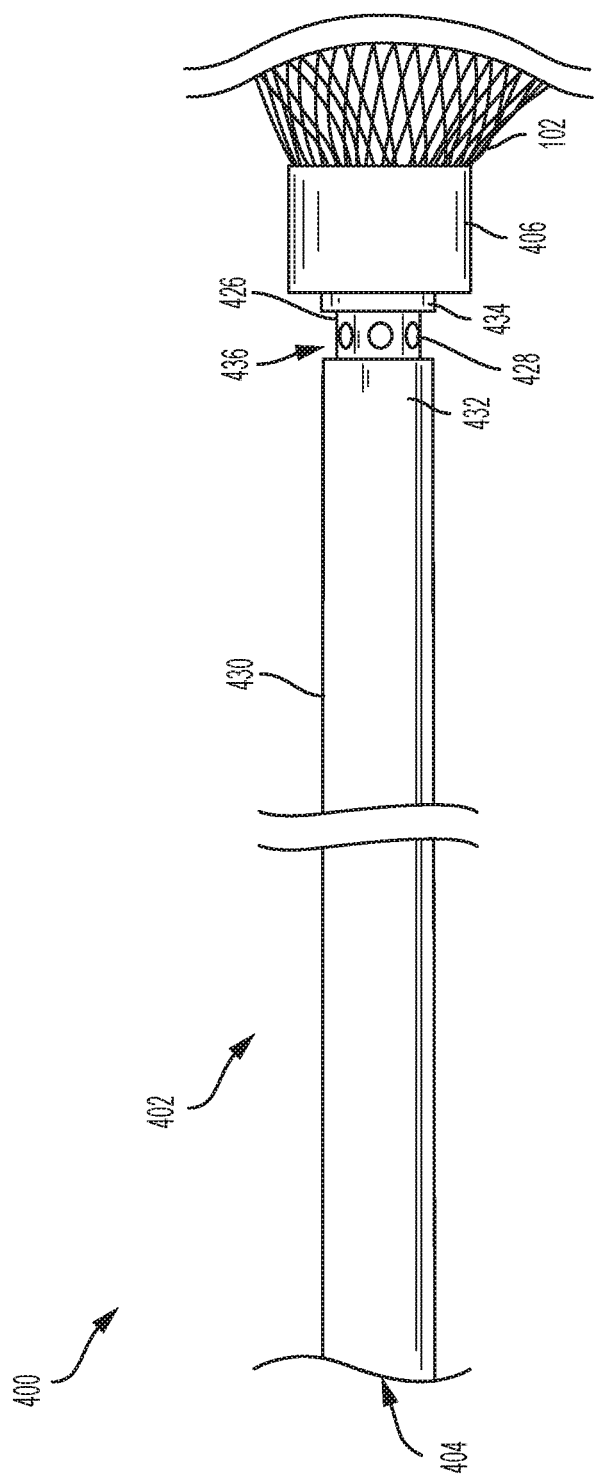
FIG. 4A shows a schematic side view of a treatment system in accordance with aspects of the present technology.
Figure 4B:
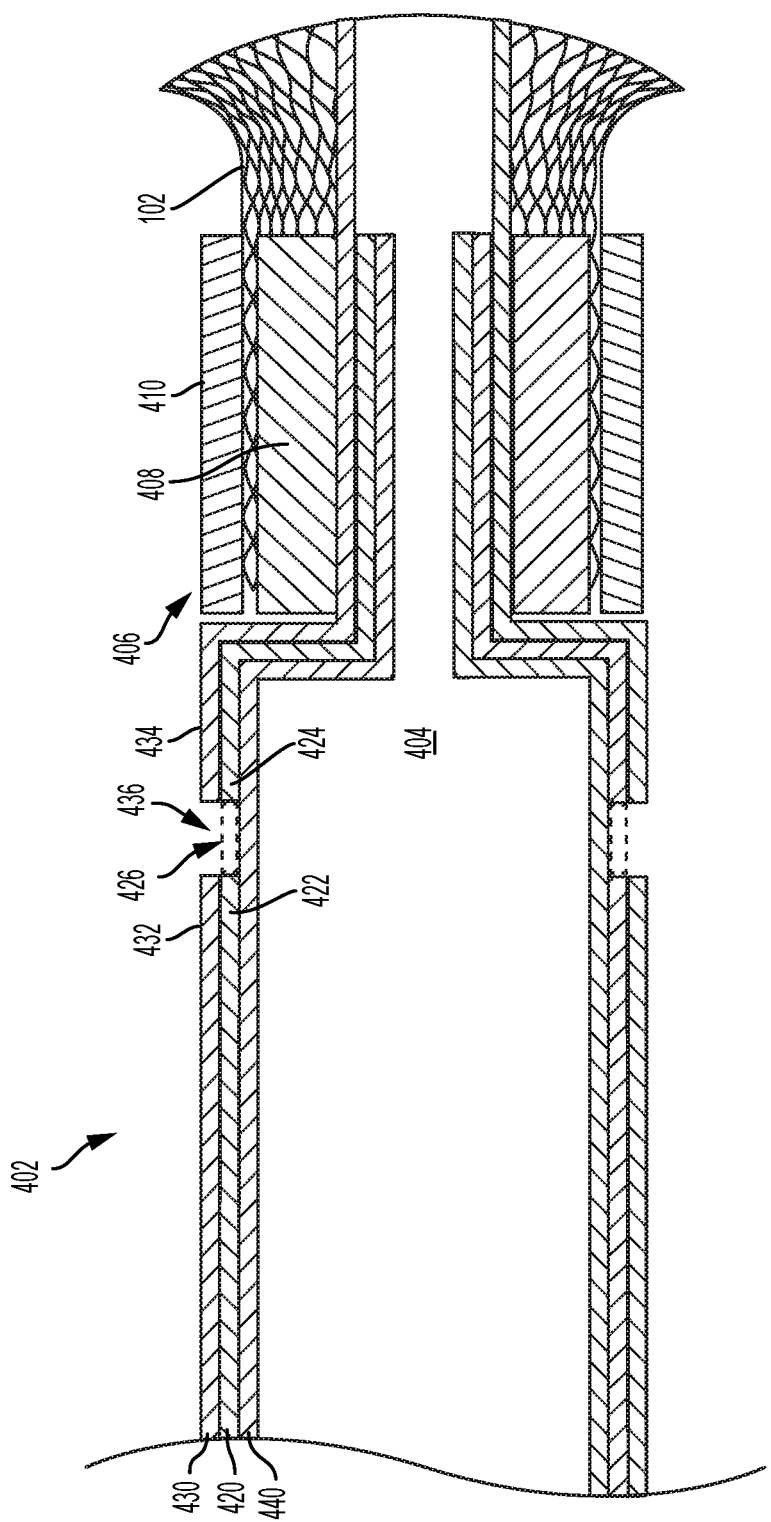
FIG. 4B shows a schematic side cross-sectional view of the treatment system shown in FIG. 4A.

FIG. 4A shows a schematic side view of a treatment system 400, and FIG. 4B shows a side cross-sectional view of a distal portion of the treatment system 400 shown in FIG. 4A. As described in more detail below, the treatment system 400 can include a conduit assembly 402 that is releasably coupled to the occlusive member 102. In operation, the treatment system 400 facilitates placement of the occlusive member 102 at the treatment site and utilizes electrolytic detachment to release the occlusive member 102 from the conduit assembly 402. As described in more detail below, a distal portion of the conduit assembly 402 may remain in place alongside the occlusive member 102 following electrolytic detachment. Furthermore, the conduit assembly 402 can facilitate introduction of an embolic element 230 (FIGS. 2-3G) therethrough for placement at the treatment site (e.g., within an aneurysm sac accompanying the occlusive member 102).

Although several examples refer to the use of electrolytic detachment, in various embodiments other techniques can be used to sever a conduit and release the occlusive member 102. For example, instead of or in addition to electrolytic detachment, embodiments of the present technology may utilize thermal detachment, mechanical detachment, chemical detachment, or any other suitable detachment techniques.

Referring to FIGS. 4A and 4B together, the conduit assembly 402 can take the form of an elongated tubular member defining a lumen 404 therein. The conduit assembly 402 can be coupled to a proximal hub 406 of the occlusive member 102, such that the lumen 404 extends distally beyond the proximal hub 406. As shown in FIG. 4B, an inner band 408 of the hub 406 circumferentially surrounds a portion of the conduit assembly 402. An outer band 410 surrounds the inner band 408, such that proximal portions of the layers of the occlusive member 102 are grasped between the inner and outer bands 408, 410 of the hub 406. Such bands can be made of any suitable material, for example being polymeric or metallic, and optionally may be radiopaque to facilitate visualization of the system 400 as it advanced through the vasculature. The bands can be crimped, with or without an adhesive or weld, to secure them in place. In operation, an embolic element can be introduced via the lumen 404 into the treatment site (e.g., within an aneurysm sac) and adjacent the occlusive member 102. In some examples, the inner band 408 can have an inner diameter of about 0.020 inches, and the outer band 410 can have an outer diameter of about 0.023 inches.

In various embodiments, the conduit assembly 402 can include a single tubular member or a plurality of tubular members arranged coaxially. Moreover, any one of the tubular members can be monolithic or can be formed of multiple separate components joined together. Additionally or alternatively, some or all of the tubular member(s) can include one or more coatings along some or all of their respective lengths. In some embodiments, one or more of the tubular members can be slidably moveable with respect to other tubular members. Alternatively or additionally, one or more of the tubular members can be fixed (e.g., non-slidably coupled) with respect to the other tubular members.

In the embodiment illustrated in FIGS. 4A-4B, the conduit assembly 402 includes a conduit 420 which takes the form of an elongated tubular member. An outer sheath 430 extends along a radially outer surface of the conduit 420, and an inner liner 440 extends along a radially inner surface of the conduit 420. As described in more detail below, the conduit 420 can include a detachment zone 426 configured to be electrolytically corroded when current is supplied to the conduit 420. The outer sheath 430 and/or the inner liner 440 can be electrically insulative such that current carried by the conduit 420 is confined to the conduit 420 and focused at the detachment zone 426. When in the presence of an electrolytic medium, such as blood, current passes from the conduit 420 to the surrounding media through the detachment zone 426.

In various embodiments, the conduit assembly 402 can have a length sufficient to permit the occlusive member 102 to be positioned at an intravascular treatment site (e.g., within an aneurysm sac) while a proximal end of the conduit assembly 402 extends outside the patient's body. For example, the conduit assembly 402 can have a length of greater than about 50 inches, 60 inches, 70 inches, or 80 inches. The conduit assembly 402 can have an outer diameter suitable to permit the assembly 402 to be slidably advanced through a delivery catheter. For example, the conduit assembly 402 can have an outer diameter of less than about 0.027 inches, less than about 0.021 inches, or less than about 0.017 inches.

In the example shown in FIGS. 4A-4B, the conduit assembly 402 extends through the hub 406 of the occlusive member 102, with a stepped down diameter at the hub 406 resulting in a narrower lumen 404 in a distal portion of the conduit assembly 402 that extends through the hub 406 and distal to the hub 406. In some embodiments, this stepped-down diameter can result from crimping the hub 406 over the conduit assembly 402. In other embodiments, however, the conduit assembly 402 need not have such a stepped-down inner and/or outer diameter. For example, the conduit assembly 402 can have an outer diameter and/or an inner diameter that is substantially constant along its length, or that tapers gradually along some or all of its length.

As noted above, the conduit assembly 402 includes a conduit 420, which can be radially disposed between an outer sheath 430 and an inner liner 440. The conduit 420 includes a proximal portion 422, a distal portion 424, and a detachment zone 426 disposed axially between the proximal portion 422 and the distal portion 424. In some embodiments, the conduit 420 can be an electrically conductive tubular member, for example a hypotube, catheter, or other suitable tubular member. In some embodiments, a portion of the conduit 420, including the detachment zone 426, can be coated with a conductive material, such as carbon, gold, platinum, tantalum, combinations thereof, and the like. One or more metallic coatings can be applied using known plating techniques. In various embodiments, the conduit 420 can have cuts (e.g., a spiral cut, a groove, etc.) along at least a portion of its length to achieve the desired mechanical properties (e.g., column strength, flexibility, kink-resistance, etc.).

The conduit 420 can be dimensioned to facilitate intravascular advancement to the treatment site and to accommodate a lumen 404 sufficient to permit advancement of embolic element(s) therethrough. In some embodiments, the conduit 420 can have a wall thickness of between about 0.0005 inches and about 0.0015 inches, or about 0.001 inches in some examples. The conduit 420 can have an outer diameter in the proximal portion of less than about 0.027 inches, less than about 0.021 inches, or less than about 0.017 inches. Additionally or alternatively, the conduit 420 can have an inner diameter of less than about 0.015 inches, less than about 0.012 inches, less than about 0.010 inches, or less than about 0.008 inches. As shown in FIG. 4B, the conduit 420 can have a stepped-down diameter where the conduit 420 passes through the hub 406. For example, the conduit 420 can have an outer diameter of about 0.016 inches proximal to the hub 406, and an outer diameter of about 0.014 inches within the hub 406. This reduced diameter can be achieved by crimping the bands of the hub 406 over the conduit 420, or by forming the conduit 420 with a stepped-down profile prior to coupling the conduit 420 to the hub 406.

The conduit 420, including the detachment zone 426, can include one or more of the following materials: ceramic materials, plastics, base metals or alloys thereof, for example stainless steel or nitinol. Some of the most suitable material combinations for forming the electrolytically corrodible points can include one or more of the following: stainless steels, preferably of the type AISI 301, 304, 316, or subgroups thereof; Ti or TiNi alloys; Co-based alloys; noble metals; or noble metal alloys, such as Pt, Pt metals, Pt alloys, Au alloys, or Sn alloys. Further, ceramic materials and plastics employed for forming the medical device can be electrically conductive.

In some embodiments, the detachment zone 426 can include features to facilitate electrolytic severability, such as features configured to reduce a time that current must be supplied to the conduit 420 before the conduit is severed at the detachment zone 426. In some embodiments, the detachment zone 426 can include a sidewall having one or more openings 428 formed therein, which can take the form of one or more windows, slits, apertures, holes, or other such features. The openings 428 can both increase the surface-area-to-volume ratio at the detachment zone 426, and can also reduce the overall amount of material forming the sidewall of the conduit 420 at the detachment zone 426. As a result, the sidewall material of the conduit 420 at the detachment zone 426 may be more readily electrolytically corroded when current is supplied to the conduit 420 and the detachment zone 426 is exposed to an electrolytic medium such as blood. Additionally or alternatively to the openings 428, the detachment zone 426 can include a reduced sidewall thickness of the conduit 420, and/or otherwise provide a lower material density than the proximal and distal portions 422, 424 of the conduit 420. In some embodiments, the detachment zone 426 can be surface treated (e.g., using laser or chemical treatment) to create a microstructure at the detachment zone 426 that differs from that of the proximal and distal portions 422, 424 of the conduit 420 to facilitate electrolytic detachment. For example, the detachment zone 426 can have a microstructure having a lower crystallinity than each of the conduit proximal portion 422 and conduit distal portion 424. As another example, the detachment zone 426 can have a microstructure that is more amorphous than each of the conduit proximal portion 422 and conduit distal portion 424.

According to some embodiments, portions of the conduit 420 can be covered with an electrically insulative material. For example, a sheath 430 that is made of or includes an electrically insulative material can extend over a radially outer surface of the conduit 420 along at least a portion of the length of the conduit 420. For example, the sheath 430 can include a proximal portion 432 that circumferentially surrounds an outer surface of the conduit proximal portion 422. The sheath 430 can also include a distal portion 434 that circumferentially surrounds an outer surface of the conduit distal portion 424. A void or gap 436 can separate the sheath proximal and distal portions 432, 434. In some embodiments, the sheath proximal and distal portions 432, 434 can be discrete members that are not connected to one another, while in other embodiments the proximal and distal portions 432, 434 may be connected across the gap 436, for example via connecting strands of material.

The sheath 430 can be fully or partially made of an electrically nonconductive or insulative polymer, such as polyimide, polypropylene, polyolefins, combinations thereof, and the like. In some embodiments, the sheath 430 takes the form of an extruded polymeric tube (e.g., PTFE), and the sheath 430 extends distally beyond the hub 406 and distally beyond a distal end of the conduit 420. Accordingly, in some embodiments, the sheath 430 can define the distal opening of the conduit assembly 402. In some embodiments, the distal end of the sheath 430 is disposed adjacent or distal to a distal end of the occlusive member 102 when the occlusive member 102 is in its expanded state. According to some embodiments, the distal end of the sheath 430 is disposed adjacent or distal to a distal end of the occlusive member 102 when the occlusive member 102 is in its low-profile state.

The sheath 430 can be dimensioned to facilitate intravascular advancement to the treatment site and to accommodate a lumen 404 sufficient to permit advancement of embolic element(s) therethrough. In some embodiments, the sheath 430 can have a wall thickness of between about 0.0005 inches and about 0.002 inches, or about 0.0015 inches in some examples. The sheath 430 can have an outer diameter in the proximal portion of less than about 0.027 inches, less than about 0.021 inches, less than about 0.017 inches, or less than about 0.015 inches. Additionally or alternatively, the sheath 430 can have an inner diameter of less than about 0.015 inches, less than about 0.012 inches, less than about 0.010 inches, or less than about 0.008 inches. As shown in FIG. 4B, the sheath 430 can have a stepped-down diameter, similar to that described above with respect to the conduit 420.

According to some embodiments, a gap 436 between the sheath proximal and distal portions 432, 434 leaves exposed the detachment zone 426 of the underlying conduit 420. When in contact with a body fluid, such as blood, the fluid serves as an electrolyte allowing current to be focused on the non-covered detachment zone 426. The sheath proximal and distal portions 422, 424 prevent exposure of the conduit proximal portion 422 and the conduit distal portion 424 to the fluid. Accordingly, electrical energy conducted along the conduit 420 is concentrated at the detachment zone 426, thereby reducing the time required to erode away the detachment zone 426. The sheath proximal and distal portions 432, 434 can be slidably disposed over, over-molded, co-extruded, sprayed on, or dip-coated with respect to the conduit 420.

The gap 436 between the sheath proximal portion 432 and the sheath distal portion 434 can be dimensioned so as to achieve the desired exposure of the underlying detachment zone 426. According to some embodiments, the gap 436 can be as small as 0.0005 inches and as large as 0.1 inches or longer. According to some embodiments, lengths of detachment zone 426 can be greater than 0.005 inches and/or less than 0.010 inches to provide sufficient exposure to achieve detachment times of less than 30 seconds.

According to some embodiments, the sheath distal portion 434 is disposed radially between the distal portion 424 of the conduit 420 and the hub 406 of the occlusive member 102. As shown in FIG. 4B, the inner band 408 of the hub 406 circumferentially surrounds and contacts the distal portion 434 of the sheath 430. The insulative sheath distal portion 434 can electrically isolate the occlusive member 102 from an electrical charge conducted along a length of the conduit 420. A proximal end of the sheath distal portion 434 may be positioned proximal to the hub 406, and a distal end of the sheath distal portion 434 may be positioned distal to the hub 406. Alternatively, the proximal end of the sheath distal portion 434 may be coterminous with a proximal end of the hub 406, and/or a distal end of the sheath distal portion 434 may be coterminous with a distal end of the hub 406.

As noted above, an inner liner 440 can be disposed radially inwardly of the conduit 420. The liner 440 can be an elongate tubular member and can be made of an electrically insulative material. In some embodiments, the liner 440 can have an inner surface defining the lumen 404 along at least a portion of the length of the conduit assembly 402. Accordingly, the inner surface of the liner 440 can be continuous and uninterrupted along its length, such that liquid embolic material passing therethrough is contained within the lumen 404 until it reaches a distal end of the liner 440. In particular, the liner 440 can provide a continuous and uninterrupted surface along the detachment zone 426 of the conduit 420, such that any embolic element(s) cannot pass from within the lumen 404 through the openings 428 in the conduit 420 at the detachment zone 426.

In various embodiments, the liner 440 can extend distally to be coterminous with the conduit 420 (e.g., at or adjacent a distal end of the hub 406), or alternatively the liner 440 can extend distally beyond the hub 406 and/or distally beyond a distal end of the conduit 420. The liner 440 can be made of or coated with a lubricious material to facilitate advancement of embolic element(s) therethrough. In some embodiments, the liner 440 takes the form of an extruded polymeric tube (e.g., PTFE) or other suitable electrically insulative material. Additionally or alternatively, the inner liner 440 can be co-extruded, sprayed on, or dip-coated with respect to the conduit 420.

The liner 440 can be dimensioned to facilitate intravascular advancement to the treatment site and to accommodate a lumen 404 sufficient to permit advancement of embolic element(s) therethrough. In some embodiments, the liner 440 can have a wall thickness of between about 0.0005 inches and about 0.0015 inches, or about 0.001 inches in some examples. The liner 440 can have an outer diameter in the proximal portion of less than about 0.027 inches, less than about 0.021 inches, or less than about 0.017 inches. Additionally or alternatively, the liner 440 can have an inner diameter of less than about 0.015 inches, less than about 0.012 inches, less than about 0.010 inches, or less than about 0.008 inches. As shown in FIG. 4B, the liner 440 can have a stepped-down diameter where the liner 440 passes through the hub 406, similar to that of the conduit 420 and sheath 430 described above.

In some embodiments, an embolic element can be delivered through the lumen 404 of the conduit assembly 402. The lumen 404 can terminate in a distal opening (not shown). As noted above, in some embodiments, the conduit assembly 402 can include an elongate flexible tubular member, for example a catheter, hypotube, polymer tube, etc. The lumen 404 can be coated with a lubricious material or lining to facilitate advancement of embolic element(s) therethrough. In some embodiments, the conduit assembly 402 is dimensioned such that the distal opening is disposed adjacent to, completely distal of, or at least partially distal of the occlusive member 102 while the occlusive member 102 is in the unexpanded state. The conduit assembly 402 can be dimensioned and configured such that the distal opening is disposed at distal to the hub 406 of the occlusive member 102, such that embolic element(s) delivered therethrough can be delivered to a region adjacent or distal of the occlusive member 102.

FIG. 4C illustrates the treatment system 400 with the conduit assembly 402 partially retracted following electrolytic severance of the conduit 420 at the detachment zone 426. As illustrated, the sheath distal portion 422 and the conduit distal portion 424 can remain coupled to the hub 406 of the occlusive member 102, while the sheath proximal portion 422, conduit distal portion 422, and the liner 440 are retracted proximally. According to some embodiments, the conduit assembly 420 can be retracted through a surrounding catheter and removed from the body completely.

Figure 5:
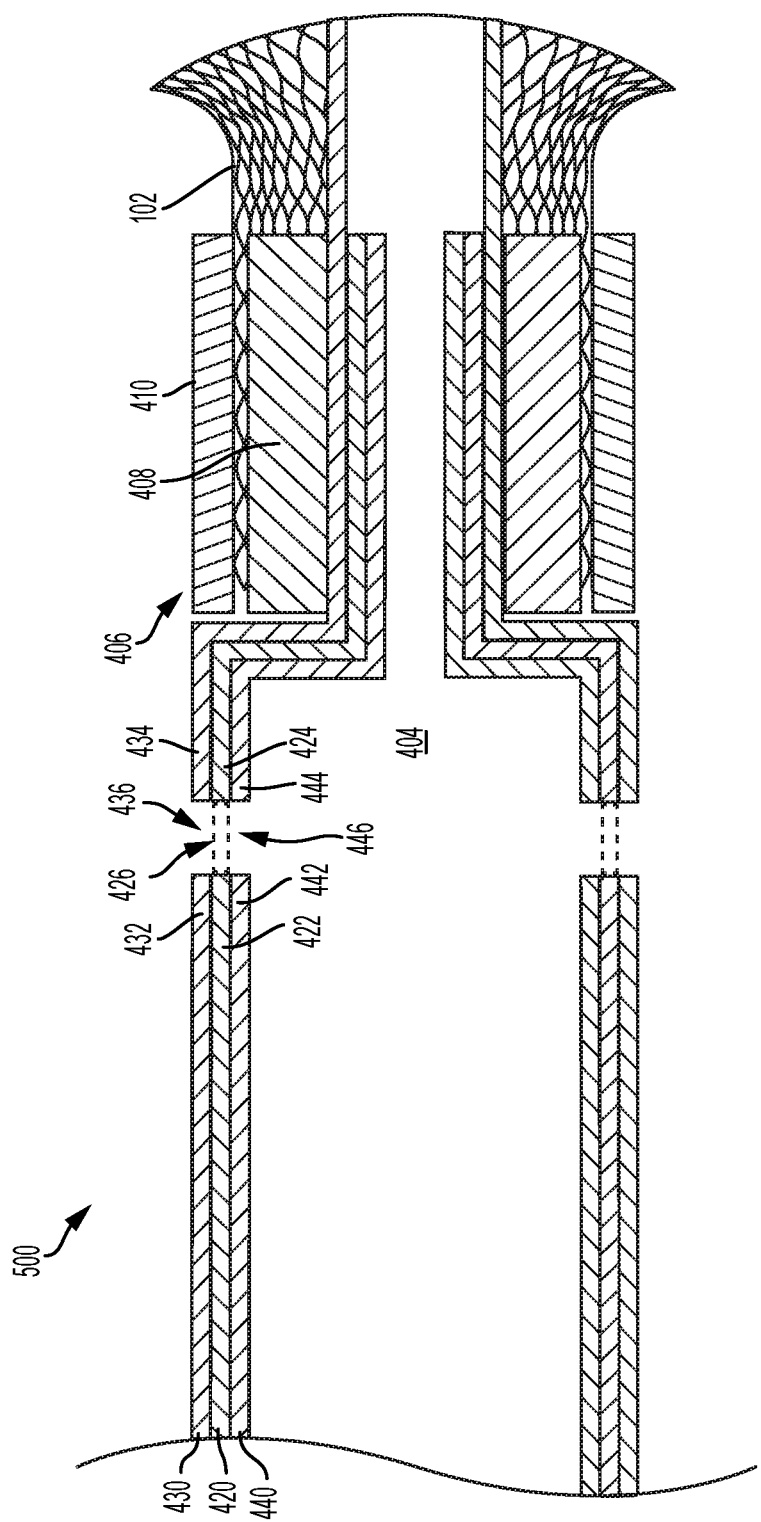
FIG. 5 shows a schematic side cross-sectional view of a portion of another embodiment of a treatment system.

FIG. 5 shows a schematic side view of another embodiment of a treatment system 500 in accordance with aspects of the present technology. The treatment system 500 can include several features that are generally similar to those of FIGS. 4A-4C described above. However, in the treatment system 500 shown in FIG. 5, the liner 440 includes a proximal portion 442 and a distal portion 424 that are spaced apart from one another by a gap 446 that is axially aligned with the detachment zone 426. In this configuration, following electrolytic severance of the conduit 420 at the detachment zone 426, the liner distal portion 444 may remain in place along with the occlusive member 102, the conduit distal portion 424, and the sheath distal portion 434. As such, the liner proximal portion 442 can be retracted along with the conduit proximal portion 422 and sheath proximal portion 432.

Figure 6:
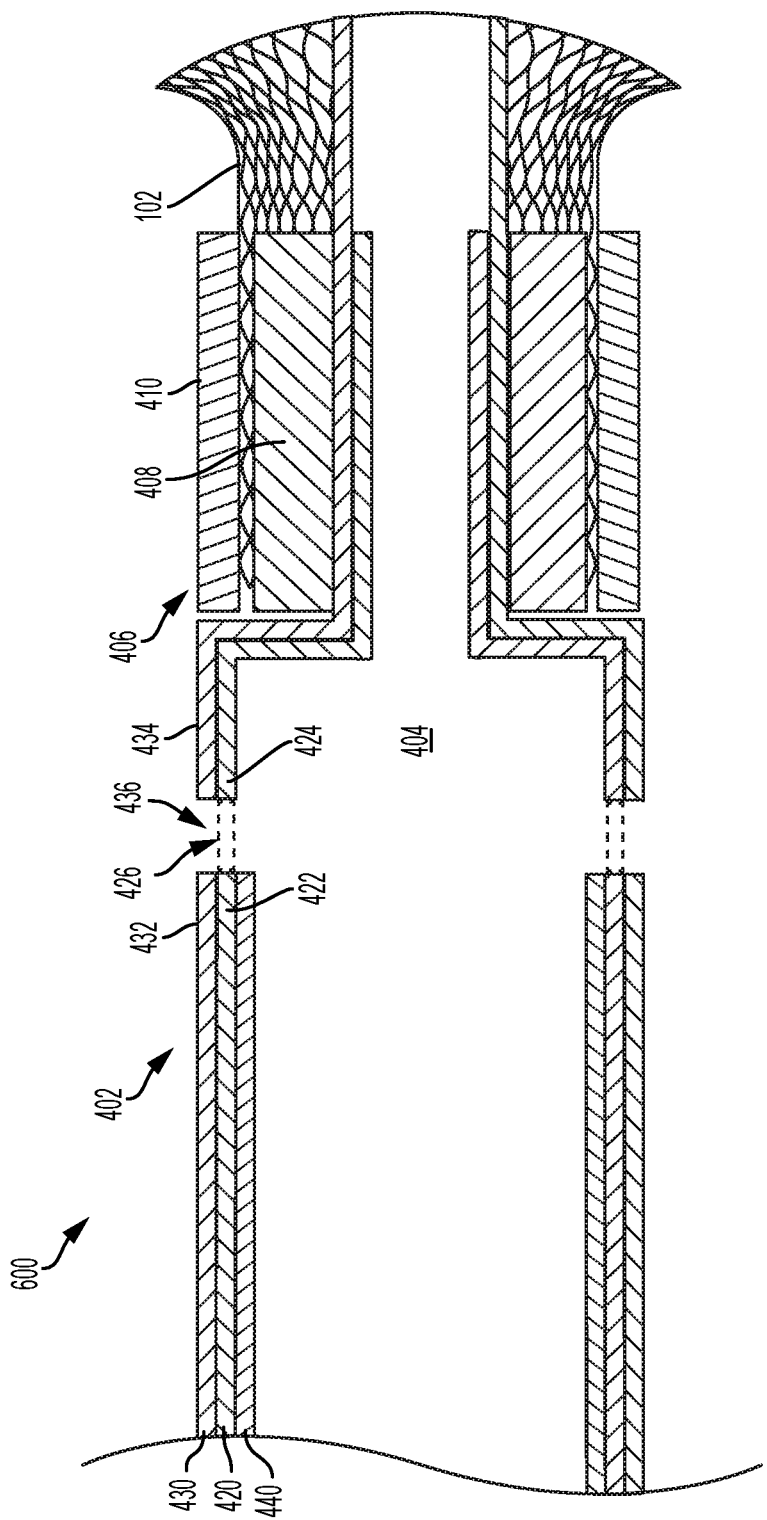
FIG. 6 shows a schematic side cross-sectional view of a portion of another embodiment of a treatment system.

FIG. 6 shows a schematic side view of another embodiment of a treatment system 600 in accordance with aspects of the present technology. The treatment system 600 can include several features that are generally similar to those of FIGS. 4A-5 described above. However, in the treatment system 600 shown in FIG. 6, the liner 440 terminates at or proximal to the detachment zone 426. In this configuration, the lumen 404 is defined by the liner 440 along a portion of the length of the treatment system 600, and is defined by the inner surface of the conduit 420 along a distal portion of the conduit assembly 402.

Figure 7:
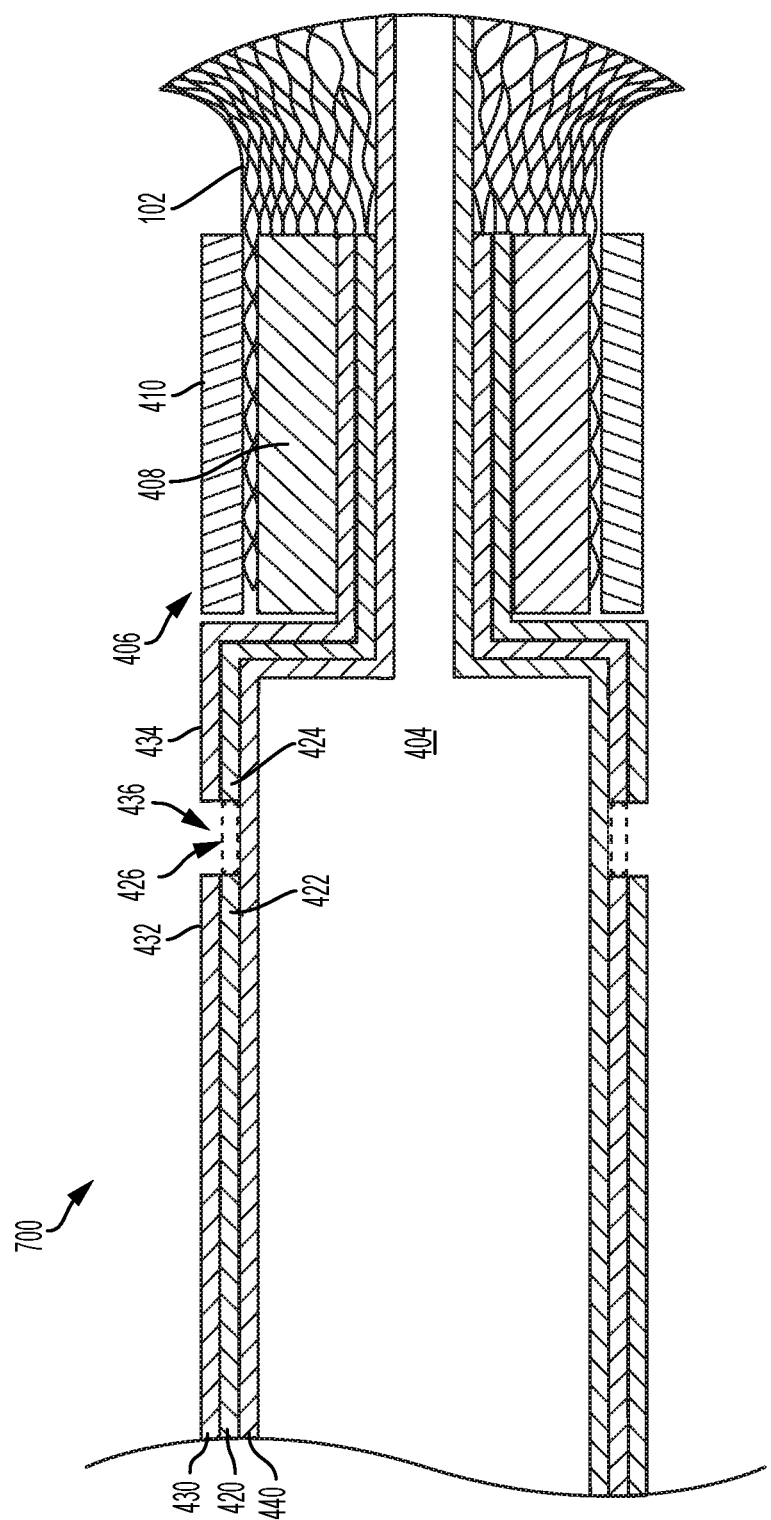
FIG. 7 shows a schematic side cross-sectional view of a portion of another embodiment of a treatment system.

FIG. 7 shows a schematic side view of another embodiment of a treatment system 700 in accordance with aspects of the present technology. The treatment system 700 can include several features that are generally similar to those of FIGS. 4A-6 described above. However, in the treatment system 700 shown in FIG. 7, the sheath 430 terminates distally at or adjacent a distal end of the hub 406. Accordingly, the sheath 430 and the conduit 420 can be substantially co-terminal. Meanwhile, the inner liner 440 can extend distally beyond the hub 406 and beyond the distal ends of the conduit 420 and sheath 430. Accordingly, in this configuration, the lumen 404 is defined along its entire length by the inner surface of the liner 440. Following severance of the conduit 420 at the detachment zone 426, the liner 440 can be proximally retracted along with the conduit proximal portion 422 and the sheath proximal portion 432. As such, following this proximal retraction, there remains no tubular member extending into an interior of the occlusive member 102, in contrast to the embodiments described above with respect to FIGS. 4A-4C. This arrangement may be beneficial if it is desirable to remove any tubular element from within the sac of the aneurysm following deployment of the occlusive member 102 and any embolic element(s).

Figure 8A:
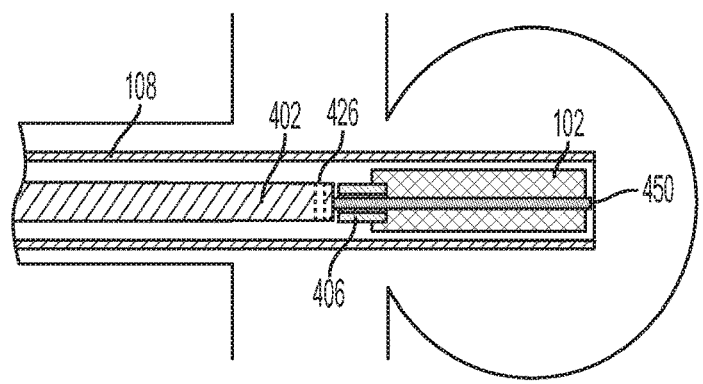
FIGS. 8A-C illustrate delivery of an occlusive member and embolic element to a treatment site in accordance with aspects of the present technology.
Figure 8B:
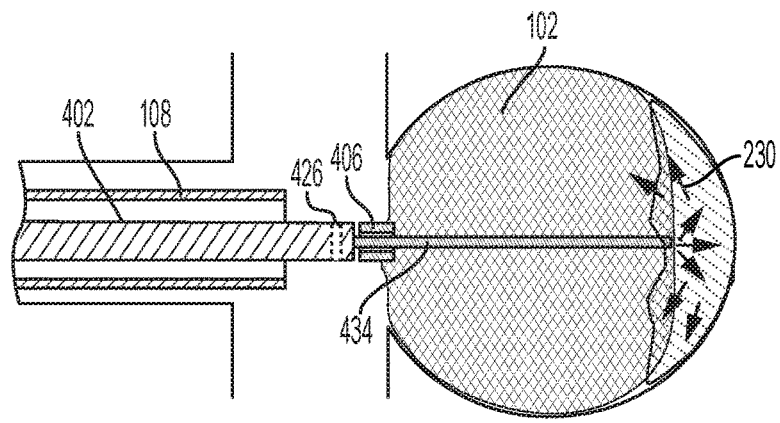
Figure 8C:
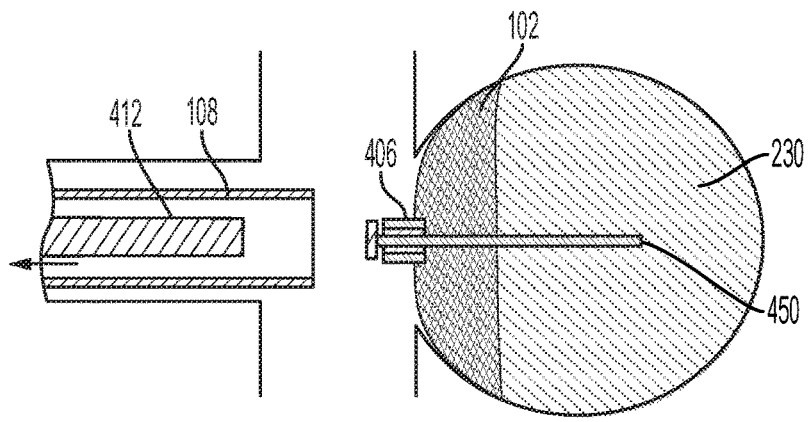

FIGS. 8A-8C illustrate delivery of an occlusive member 102 and embolic element 230 to a treatment site within an aneurysm sac. As shown in FIG. 8A, the treatment system 400 can be positioned within a second elongate shaft 108 (e.g., a microcatheter) for intravascular advancement until the microcatheter is at or adjacent to the aneurysm sac. In the illustrated embodiment, the distal end of the second elongate shaft 108 extends within the aneurysm sac, however in other embodiments the distal end of the second elongate shaft 108 can be positioned at the neck of the aneurysm or proximal to the neck of the aneurysm.

In the position shown in FIG. 8A, the system 400 has been advanced within the elongate shaft 108 such that the occlusive member 102 remains in a constrained, low-profile configuration within the shaft 108 while at least a portion of the conduit assembly 402 extends adjacent to the occlusive member 102 and within the shaft 108. In various embodiments, the shaft 108 can have an inner diameter of about 0.017 inches or less, about 0.021 inches or less, or about 0.027 inches or less.

As shown in FIG. 8B, once the distal opening 450 of the conduit assembly 402 is positioned at or near the treatment site (e.g., within the aneurysm sac), the elongate shaft 108 can be retracted, thereby deploying the occlusive member 102 within the aneurysm sac (e.g., allowing the occlusive member 102 to self-expand). In this position, the embolic element 230 can be advanced through the conduit assembly 402 and into the aneurysm to a region distal to the occlusive member 102. In the case of a fluid or gel, a syringe or other injector may be used to urge the embolic element 230 through the lumen 404. In the case of microcoils or other structural embolic element(s), a delivery wire or other suitable mechanism may be slidably advanced through the lumen 404 of the conduit assembly 402 to position the embolic element 230 into the aneurysm sac.

As described previously with respect to FIGS. 3A-3G, introduction of the embolic element 230 can cause the occlusive member 102 to deform, for example to at least partially fold in on itself to provide for increased protection in a neck region of the aneurysm. Once the embolic element 230 been delivered and the occlusive member 102 has deformed, the occlusive member 102 can be severed from the conduit assembly 402 as described above. For example, a power supply or other current source can be used to generate current through the conduit 420, resulting in electrolytic corrosion of the conduit 420 at the detachment zone 426.

As shown in FIG. 8C, after the occlusive member 102 is released via electrolytic corrosion of the detachment zone 426, the conduit assembly 402 can be proximally retracted while the occlusive member 102 and the embolic element 230 remain positioned within the aneurysm. As the conduit assembly 402 is retracted, the distal portion of the conduit assembly (e.g., the distal portion 434 of the sheath 430 and/or the distal portion 424 of the conduit 420) can remain within the aneurysm and coupled to the occlusive member 102.

IV. CONCLUSION

Although many of the embodiments are described above with respect to systems and methods related to treatment of hemorrhagic stroke, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-8C.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Unless otherwise indicated, all numbers expressing dimensions, percentages, or other numerical values used in the specification and claims, are to be understood as being modified in all instances by the term "about." Accordingly, unless indicated to the contrary, the numerical parameters set forth in the specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A treatment system comprising:
   an electrolytically corrodible conduit comprising:
   a proximal portion, a distal portion, and a detachment zone between the proximal portion and the distal portion, wherein the detachment zone includes a sidewall having one or more apertures formed therein; and
   a first lumen defined by the sidewall and in communication with the one or more apertures;
   an expandable occlusive member having a proximal hub coupled to the conduit distal portion and a distal opening at a distal portion of the occlusive member, the occlusive member configured to be positioned at an intrasaccular treatment site; and
   a liner disposed within the first lumen of the conduit and coving the one or more apertures, the liner defining a second lumen configured to pass an embolic element therethrough, the liner having a distal end that extends distally through the distal opening of the occlusive member.

2. The treatment system of claim 1, wherein the detachment zone comprises a portion of the conduit configured to be severed in response to delivery of electrical current thereto.

3. The treatment system of claim 1, wherein the liner is configured to be slidably retracted with respect to the occlusive member following severance of the detachment zone.

4. The treatment system of claim 1, wherein the embolic element is a liquid embolic.

5. The treatment system of claim 1, further comprising an electrically insulative sheath extending over the conduit, wherein the sheath does not extend fully over the detachment zone.

6. A treatment system comprising:
   a conduit having a sidewall defining a first lumen configured to pass an embolic element therethrough, the conduit having a proximal portion, a distal portion, and an electrolytically corrodible detachment zone between the proximal portion and the distal portion;
   an occlusive member coupled to the conduit distal portion, the occlusive member configured to be positioned at or adjacent to a treatment site, the occlusive member comprising a distal opening at a distal portion of the occlusive member, and
   an inner tubular member disposed within the first lumen of the conduit and covering the detachment zone, the tubular member defining a second lumen configured to pass an embolic element therethrough, the tubular member having a distal end that extends distally through the distal opening of the occlusive member.

7. The treatment system of claim 6, wherein the conduit sidewall has a reduced thickness in the detachment zone.

8. The treatment system of claim 6, wherein the occlusive member comprises an intrasaccular device configured to be implanted within an aneurysm.

9. The treatment system of claim 6, wherein the inner tubular member is configured to be slidably retracted with respect to the occlusive member following severance of the detachment zone.

10. The treatment system of claim 6, wherein the embolic element is a liquid embolic.

11. The treatment system of claim 6, further comprising an electrically insulative sheath extending over the conduit, wherein the sheath does not extend fully over the detachment zone.

12. A treatment system comprising:
    a first tubular member comprising:
    a sidewall defining a lumen; and
    a detachment zone including one or more apertures formed in the sidewall;
    a second tubular member disposed within the lumen of the first tubular member, the second tubular member having a sidewall that is continuous along at least the detachment zone and covers the one or more apertures while the second tubular member is in a delivery configuration with respect to the first tubular member; and
    an implant coupled to the first tubular member at a position distal to the detachment zone, wherein a distal end of the second tubular member extends distally through a distal opening of the implant.

13. The treatment system of claim 12, wherein the second tubular member defines a second lumen configured to pass an embolic material therethrough.

14. The treatment system of claim 12, wherein the implant is an intrasaccular device configured to be implanted within an aneurysm.

15. The treatment system of claim 12, wherein the detachment zone comprises a portion of the first tubular member configured to be severed in response to delivery of electrical current thereto.

16. The treatment system of claim 12, wherein the second tubular member is configured to be slidably retracted with respect to the implant following severance of the detachment zone.

* * * * *

UNITED STATES PATENT AND TRADEMARK OFFICE
CERTIFICATE OF CORRECTION

| | |
|---|---|
| PATENT NO. | : 11,504,816 B2 |
| APPLICATION NO. | : 16/949566 |
| DATED | : November 22, 2022 |
| INVENTOR(S) | : Nguyen et al. |

It is certified that error appears in the above-identified patent and that said Letters Patent is hereby corrected as shown below:

In the Claims

In Column 31, in Claim 1, Line 30, delete "coving" and insert -- covering --, therefor.

In Column 32, in Claim 6, Line 3, delete "member," and insert -- member; --, therefor.

Signed and Sealed this
Third Day of January, 2023

Katherine Kelly Vidal
*Director of the United States Patent and Trademark Office*